US012673968B2

(12) United States Patent
McInroy et al.

(10) Patent No.: US 12,673,968 B2
(45) Date of Patent: Jul. 7, 2026

(54) MODIFIED GUANINES

(71) Applicant: NUCLERA LTD, Cambridge (GB)

(72) Inventors: Gordon Ross McInroy, Cambridge (GB); Martin Edward Fox, Cambridge (GB); Puneet Srivastava, Cambridge (GB); Michal Robert Matuszewski, Cambridge (GB)

(73) Assignee: NUCLERA LTD, Cambridge (GB)

( * ) Notice: Subject to any disclaimer, the term of this patent is extended or adjusted under 35 U.S.C. 154(b) by 505 days.

(21) Appl. No.: 18/277,642

(22) PCT Filed: Feb. 21, 2022

(86) PCT No.: PCT/GB2022/050463
§ 371 (c)(1),
(2) Date: Aug. 17, 2023

(87) PCT Pub. No.: WO2022/175685
PCT Pub. Date: Aug. 25, 2022

(65) Prior Publication Data

US 2024/0150389 A1 May 9, 2024

(30) Foreign Application Priority Data

Feb. 19, 2021 (GB) ..................................... 2102381

(51) Int. Cl.
*C07H 19/14* (2006.01)

(52) U.S. Cl.
CPC .................................... *C07H 19/14* (2013.01)

(58) Field of Classification Search
None
See application file for complete search history.

(56) References Cited

U.S. PATENT DOCUMENTS

| | | | |
|---|---|---|---|
| 8,034,923 B1 | 10/2011 | Benner et al. |
| 10,654,841 B1 | 5/2020 | Benner et al. |
| 2011/0275124 A1 | 11/2011 | Benner et al. |
| 2016/0326517 A1 | 11/2016 | Gurnett et al. |
| 2018/0265537 A1 | 9/2018 | Benner |

FOREIGN PATENT DOCUMENTS

| | | |
|---|---|---|
| GB | 2553274 A | 3/2018 |
| WO | 2010110775 A1 | 9/2010 |
| WO | 2016/128731 A | 8/2016 |
| WO | 2016/139477 A1 | 9/2016 |
| WO | 2017/009663 A1 | 1/2017 |
| WO | 2017058953 A1 | 4/2017 |
| WO | 2019/053443 A1 | 3/2019 |
| WO | 2019/097233 A1 | 5/2019 |

OTHER PUBLICATIONS

Lakshman M.K. et al., "Azide-Tetrazole Equilibrium of C-6 Azidopurine Nucleosides and Their Ligation Reactions With Alkynes", J Org Chem 75(8):2461-2473 (Apr. 16, 2010).
Ramzaeva N. et al., "Facile Synthesis of 2'-Deoxynucleoside Analogs of PreQ", Synthesis 9:1327-1330 (Sep. 1998).
Seela F. et al., "Liquid-Liquid and Solid-Liquid Phase-Transfer Glycosylation of Pyrrolo[2,3-d]-Pyrimidines: Stereospecific Synthesis of 2-Deoxy-β-D-Ribofuranosides Related to 2'-Deoxy-7-Carbaguanosine", J. Chem. Soc. Perkin Trans 1:697-702 (1988).
International Search Report and Written Opinion of the International Searching Authority dated Jun. 10, 2022 received in PCT/GB2022/050463.
Great Britain Search Report dated Jul. 6, 2021 received in GB2102381.7.
Hutter, D., et al., "Labeled Nucleoside Triphosphates with Reversibly Terminating Aminoalkoxyl Groups", Nucleosides, Nucleotides & Nucleaic Acids, vol. 29, No. 11-12, Nov. 30, 30, 2020, pp. 879-895, XP055010178.
Chen, F., et al., "Reconstructed evolutionary adaptive paths give polymerases accepting reversible terminators for sequencing SNP detection", Proceedings of the National Academy of Sciences of the United States of America, 1948-1953, vol. 107(5), 2010, pp. S1948/1-S1948/32, ISSN: 0027-8424.

*Primary Examiner* — Dale R Miller
(74) *Attorney, Agent, or Firm* — Scully, Scott, Murphy & Presser, P.C.

(57) ABSTRACT

The present invention relates to a compound according to Formula (1a) or (1b):

(1a)

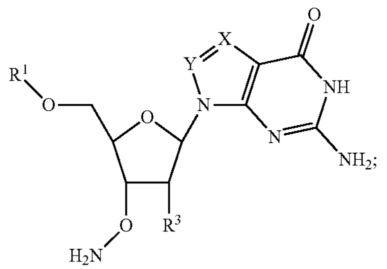

(1b)

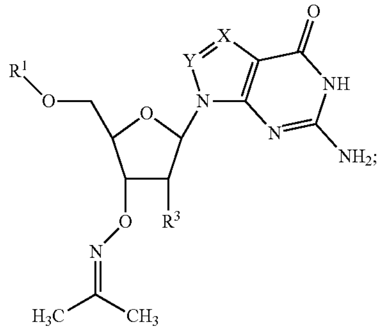

wherein $R^1$; $R^3$; Y and X are defined herein, and their use in methods of nucleic acid synthesis.

18 Claims, 13 Drawing Sheets

Fig, 8

MODIFIED GUANINES

FIELD OF THE INVENTION

The invention relates to modified purine nucleotides having an electron withdrawing group added at the 7- or 8-position. The invention also relates to a method of nucleic acid synthesis to produce oligonucleotides containing said modified purine nucleotide. The invention further relates to a kit comprising the modified purine, a terminal transferase enzyme and optionally a salt.

BACKGROUND TO THE INVENTION

Nucleic acid synthesis is vital to modern biotechnology. The rapid pace of development in the biotechnology arena has been made possible by the scientific community's ability to artificially synthesise DNA, RNA and proteins.

Artificial DNA synthesis allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. Despite being a mature technology, it is highly challenging to synthesise a DNA strand greater than 200 nucleotides in length in viable yield, and most DNA synthesis companies only offer up to 120 nucleotides routinely. In comparison, an average protein-coding gene is of the order of 2000-3000 contiguous nucleotides, a chromosome is at least a million contiguous nucleotides in length and an average eukaryotic genome numbers in the billions of nucleotides. In order to prepare nucleic acid strands thousands of base pairs in length, all major gene synthesis companies today rely on variations of a 'synthesise and stitch' technique, where overlapping 40-60-mer fragments are synthesised and stitched together by enzymatic copying and extension. Current methods generally allow up to 3 kb in length for routine production.

The reason DNA cannot be routinely synthesised beyond 120-200 nucleotides at a time is due to the current methodology for generating DNA, which uses synthetic chemistry (i.e., phosphoramidite technology) to couple a nucleotide one at a time to make DNA. Even if the efficiency of each nucleotide-coupling step is 99% efficient, it is mathematically impossible to synthesise DNA longer than 200 nucleotides in acceptable yields. The Venter Institute illustrated this laborious process by spending 4 years and 20 million USD to synthesise the relatively small genome of a bacterium.

Known methods of DNA sequencing use template-dependent DNA polymerases to add 3'-reversibly terminated nucleotides to a growing double-stranded substrate. In the 'sequencing-by-synthesis' process, each added nucleotide contains a dye, allowing the user to identify the exact sequence of the template strand. Albeit on double-stranded DNA, this technology is able to produce strands of between 500-1000 bps long. However, this technology is not suitable for de novo nucleic acid synthesis because of the requirement for an existing nucleic acid strand to act as a template.

Various attempts have been made to use a terminal deoxynucleotidyl transferase for de novo single-stranded DNA synthesis. Uncontrolled de novo single stranded DNA synthesis, as opposed to controlled, takes advantage of TdT's deoxynucleoside triphosphate (dNTP) 3' tailing properties on single-stranded DNA to create, for example, homopolymeric adaptor sequences for next-generation sequencing library preparation. In controlled extensions, a reversible deoxynucleoside triphosphate termination technology needs to be employed to prevent uncontrolled addition of dNTPs to the 3'-end of a growing DNA strand. The development of a controlled single-stranded DNA synthesis process through TdT would be invaluable to in situ DNA synthesis for gene assembly or hybridization microarrays as it removes the need for an anhydrous environment and allows the use of various polymers incompatible with organic solvents.

However, TdT has been shown not to efficiently add nucleoside triphosphates containing 3'-O-reversibly terminating moieties for building up a nascent single-stranded DNA chain necessary for a de novo synthesis cycle. A 3'-O-reversible terminating moiety would prevent a terminal transferase such as TdT from catalysing the nucleotide transferase reaction between the 3'-end of a growing DNA strand and the 5'-triphosphate of an incoming nucleoside triphosphate. The inventors have previously discovered certain modified nucleotides can be incorporated using terminal transferases. Modified nucleotides suitable for terminal transferase extension have been disclosed in for example PCT/GB2018/053305. A common reversible terminator is the aminooxy (O—$NH_2$) group. The aminooxy group is converted to OH by treatment with nitrite. However, the purine nucleobase guanine carries an exocyclic $NH_2$ group that is also susceptible to reaction with nitrite. Reaction with nitrite leads to deamination, that is, conversion of the exocyclic amine into a carbonyl. This chemical reaction introduces a mutation into the oligonucleotide, for example, deamination of guanine gives rise to the nucleoside xanthine, a base that can base pair to T rather than C, therefore introducing a mutation.

Purines are one of two classes of heterocyclic nitrogenous bases found in both DNA and RNA nucleic acid constructs. Purines found in DNA and RNA nitrogenous bases are adenine (A) and guanine (G).

These bases can form hydrogen bonds with their complementary pyrimidines—cytosine (C) in the case of guanine and thymine (T) (DNA) or uracil (U) (RNA) in the case of adenine. Hydrogen bonding is of vital biochemical importance, for instance it is required to form complementary double stranded structures or select the correct tRNAs during protein translation.

Deamination changes the hydrogen bonding pattern of the base and thus alters the base pairing properties of the base. One effect of a deamination mutation is to change the efficiency with which a nucleic acid can hybridise to a target; this effect typically manifests in a decrease in the melting temperature of the duplex. A second effect of a deamination mutation is that a nucleic acid copy (for instance made by a DNA polymerase) will also contain a mutation. A third effect of a deamination mutation is to change the function of the nucleic acid, for example, by changing the amino acid sequence of a resultant peptide/protein should the nucleic acid undergo translation. The protein translated from a mutated nucleic acid would have the wrong sequence, likely fold incorrectly, and ultimately exhibit a loss of or reduction in function. Clearly, mutations are often unacceptable as they affect the properties of the nucleic acid and lead to a change in the encoded information.

SUMMARY OF THE INVENTION

Disclosed herein a method of reducing the deamination of the guanine base during oligonucleotide synthesis. The method is particularly applicable when nitrite is used to remove an aminooxy terminating moiety from the sugar hydroxyl.

An aspect of the present invention relates to a compound according to Formula (1a) or (1b):

(1a)

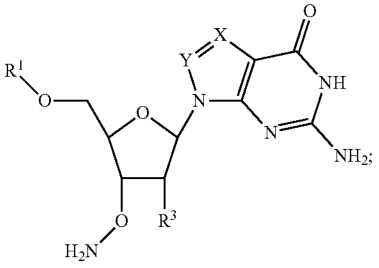

(1b)

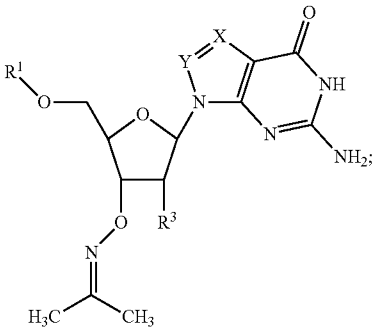

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

A further aspect of the present invention relates to a compound according to Formula (1a) or (1b):

(1a)

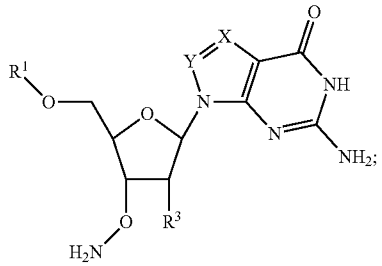

(1b)

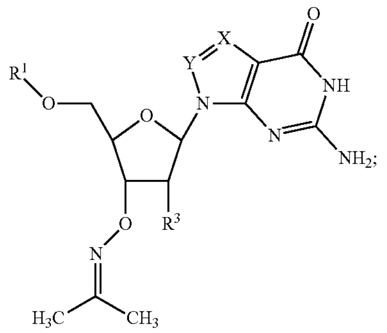

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: nitrile; halomethyl, dihalomethyl, trihalomethyl; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

A further aspect of the present invention relates to a method of nucleic acid synthesis comprising reacting a compound of Formula (1a) or (1b) with an oligonucleotide in the presence of a nucleic acid polymerizing enzyme, for example a DNA polymerase or terminal deoxynucleotidyl transferase (TdT) enzyme and treating the extended oligonucleotide with a nitrite salt.

A further aspect of the present invention relates to a kit comprising:

(i) a compound according to any one of Formula (1a) or (1b);

(ii) a terminal deoxynucleotidyl transferase (TdT) enzyme; and optionally (iii) a nitrite salt.

A further aspect of the present invention relates to an oligonucleotide according to Formula (1a) or (1b):

(1a)

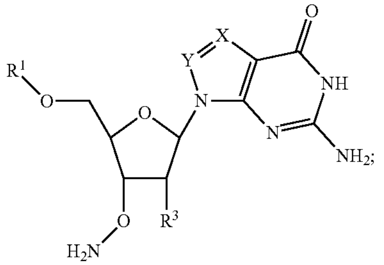

(1b)

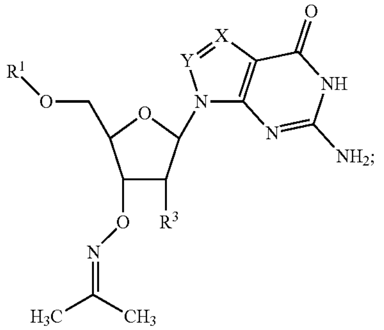

wherein, $R^1$ is an oligonucleotide;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

DETAILED DESCRIPTION OF THE INVENTION

Disclosed herein is a method of reducing the deamination of the guanine base during oligonucleotide synthesis. The method is particularly applicable when nitrite is used to convert an aminooxy terminating moiety on the sugar to a hydroxyl. Electron withdrawing groups (EWG) in the 7- or 8-position of guanine can dramatically reduce nitrosative deamination. These EWG in the 7- or 8-position can increase the stability of guanine molecules relative to the parent compound. In particular, chloro, fluoro and trifluoromethyl substituents at the 7-position decrease the rate of nitrite-mediated deamination by up to an order of magnitude. There is a significant industrial applicability because deamination changes the identity and hydrogen bonding pattern of the base, i.e. deamination introduces mutations into the product. Mutations are undesirable as they lead to change in sequence of the DNA, and thus affect the biophysical properties, biochemical properties, and information encoding properties of the DNA.

7- or 8-position modified guanine nucleotides are of value to enzymatic DNA synthesis when using 3'-O-aminooxy reversible terminators or the precursors thereof. While guanine present in a synthesised strand will undergo a level of nitrite-mediated deamination that introduces mutations, 7- or 8-position electron withdrawing modified adenines are more robust and thus yield a higher quality product.

The 3'-O-aminooxy reversible terminator precursors may include where the aminooxy is protected as an oxime, for example $N{=}C(CH_3)_2$. The oxime can be transformed into aminooxy as part of the unblocking process.

As guanine and cytosine form three hydrogen bonds, while thymidine and adenine form only two hydrogen bonds, the GC base pair is stronger than the AT base pair. As a result, GC rich regions typically have a high melting temperature (Tm) and are prone to forming secondary structures such as hairpin loops and G-quadruplexes. Secondary structure can be deleterious for enzymatic DNA synthesis as terminal transferases require access to the 3'-terminal end in single stranded or single strand overhang form for optimal activity. 7- or 8-position modifications of guanine can be used to tune the hydrogen bond strength of the GC base pair. As such, 7- or 8-position modified guanine can result in a weaker hydrogen bond and reduced secondary structure, which can improve enzymatic DNA synthesis.

An aspect of the present invention relates to a compound according to Formula (1a) or (1b):

(1a)

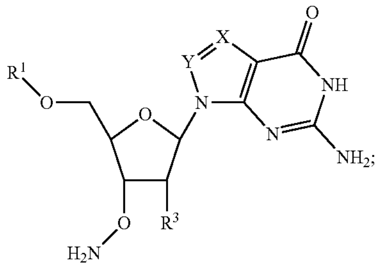

(1b)

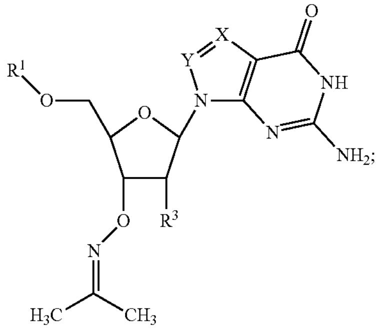

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

An aspect of the invention involves converting compounds of Formula (1b) to compounds of Formula (1a). The conversion may be performed using aminooxy compounds. The conversion may be performed using methoxylamine. Disclosed is a method of synthesizing a compound according to formula (1a):

(1a)

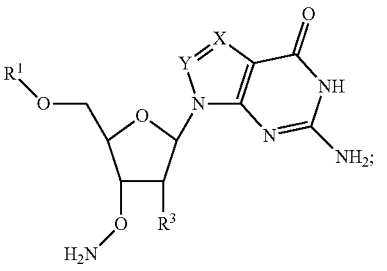

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms;

using a compound according to Formula (1b):

(1b)

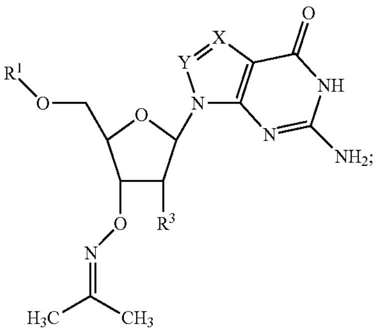

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

Disclosed is a compound according to Formula (1a) or (1b):

(1a)

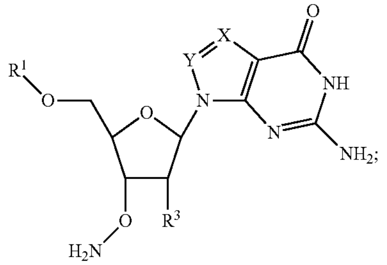

(1b)

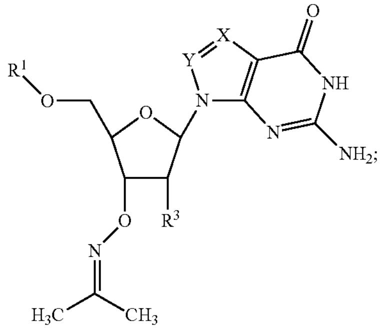

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: nitrile; halomethyl, dihalomethyl, trihalomethyl; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

Disclosed is a method of synthesizing a compound according to formula (1a):

(1a)

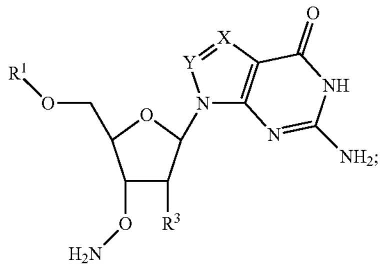

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; C≡CR$^4$; SOR$^4$; $SO_2R^4$; $SO_3R^4$; COR$^4$; $CO_2R^4$; CONR$^4$R$^5$;

wherein $R^4$ and $R^5$ are independently selected from H and $C_{1-6}$ alkyl optionally substituted with OH or halo atoms;

comprising taking a compound according to Formula (1b):

(1b)

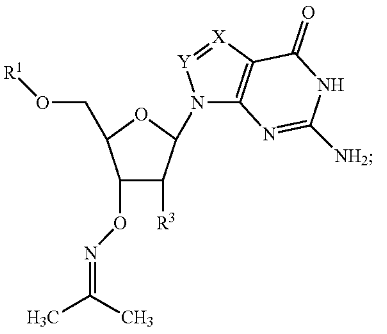

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is CR$^2$ and Y is CH or N, where $R^2$ is an electron withdrawing group (EWG) selected from the group consisting of: halo; nitro, nitrosyl, nitrile; halomethyl, dihalomethyl, trihalomethyl; C≡CR$^4$; SOR$^4$; $SO_2R^4$; $SO_3R^4$; COR$^4$; $CO_2R^4$; CONR$^4$R$^5$;

wherein $R^4$ and $R^5$ are independently selected from H and $C_{1-6}$ alkyl optionally substituted with OH or halo atoms;

and treating the compounds of Formula (1b) with an aminooxy compound.

The aminoxy compound may be hydroxylamine, methoxylamine or ethoxylamine.

$R^1$ can be a phosphate or polyphosphate group. The phosphate groups can be protonated or in salt form. The phosphates can be entirely oxygen, or can contain one or more sulfur atoms. $R^1$ can be a phosphate group. $R^1$ can be a polyphosphate group. $R^1$ can also be a phosphate or polyphosphate group selected from $—(PO_3)^-_x(PO_2S)^-_y(PO_3)^-_z$ where x, y and z are independently 0-5 and x+y+z is 1-5. $R^1$ can also be a phosphate or polyphosphate group having one or more sulfur atoms. $R^1$ can be a phosphate group having one or more sulfur atoms. $R^1$ can be a polyphosphate group having one or more sulfur atoms. The sulfur atom can be in any position on any on the phosphate groups. $R^1$ can further be a monophosphate, diphosphate, triphosphate, tetraphosphate, pentaphosphate, or (alpha-thio)triphosphate group. $R^1$ can be a monophosphate group. $R^1$ can be a diphosphate group. $R^1$ can be a tetraphosphate group. $R^1$ can be a pentaphosphate group. $R^1$ can be an (alpha-thio)triphosphate group. $R^1$ can be a triphosphate group. $R^1$ can be an oligonucleotide.

$R^2$ is an electron withdrawing group (EWG). $R^2$ can be an electron withdrawing group (EWG) that can be selected from the group consisting of halo; nitro, nitrosyl, nitrile; halomethyl, dihalomethyl, trihalomethyl; C≡CR$^4$; SOR$^4$; $SO_2R^4$; $SO_3R^4$; COR$^4$; $CO_2R^4$; CONR$^4$R$^5$. $R^2$ can be a halo group. $R^2$ can be selected from F, Cl, Br or I. $R^2$ can be F or Cl. $R^2$ can be a nitrile group. $R^2$ can be a nitro group. $R^2$ can be a nitrosyl group. $R^2$ can be halo, halomethyl, dihalomethyl or trihalomethyl. $R^2$ can be a halomethyl group. $R^2$ can be a dihalomethyl group. $R^2$ can be a trihalomethyl group. $R^2$ can be a C≡CR$^4$ group. $R^2$ can be a SOR$^4$; $SO_2R^4$ or $SO_3R^4$ group. $R^2$ can be an electron withdrawing group (EWG) consisting of a COR$^4$ group such as an aldehyde or ketone. $R^2$ can be an electron withdrawing group (EWG) consisting of a $CO_2R^4$ group such as an acid or ester. $R^2$ can be an electron withdrawing group (EWG) consisting of an amide CONR$^4$R$^5$ group.

$R^4$ and $R^5$ can be independently selected from H and $C_{1-6}$ alkyl optionally substituted with OH or halo atoms. $R^4$ and $R^5$ can be independently selected from H and $C_{1-6}$ alkyl optionally substituted with OH or 1-6 halo atoms. $R^4$ can be H. $R^4$ can be $C_{1-6}$ alkyl optionally substituted with OH or halo atoms, wherein the halo atoms can be selected from F, Cl, Br or I. $R^4$ can be $C_{1-6}$ alkyl optionally substituted with OH or 1-6 halo atoms, wherein the halo atoms can be selected from F, Cl, Br or I. $R^4$ can be $CH_3$. $R^4$ can be $CH_2OH$. $R^4$ can be $CH_2CH_2OH$.

$R^5$ can be H. $R^5$ can be $C_{1-6}$ alkyl optionally substituted with OH or halo atoms. $R^5$ can be $C_{1-6}$ alkyl optionally substituted with OH or 1-6 halo atoms. $R^5$ can be $C_{1-6}$ alkyl optionally substituted with OH or halo atoms, wherein the halo atoms can be selected from F, Cl, Br or I. $R^5$ can be $C_{1-6}$ alkyl optionally substituted with OH or 1-6 halo atoms, wherein the halo atoms can be selected from F, Cl, Br or I. $R^5$ can be $CH_3$.

One embodiment of the present invention relates to a compound according to Formula (1a) or (1b) wherein $R^2$ can be selected from the group consisting of fluoro, chloro or trifluoromethyl. $R^2$ can be fluoro. $R^2$ can be chloro. $R^2$ can be $CF_3$. $R^2$ can be absent where Y and X are both N.

$R^3$ can be selected from H, OH, F, $OCH_3$ or $OCH_2CH_2OMe$. $R^3$ can be OH. $R^3$ can be F. $R^3$ can be $OCH_3$. $R^3$ can be $OCH_2CH_2OMe$. Preferably, $R^3$ can be H.

The compounds of Formula (1a) or (1b) can be selected from the group consisting of:

(a)

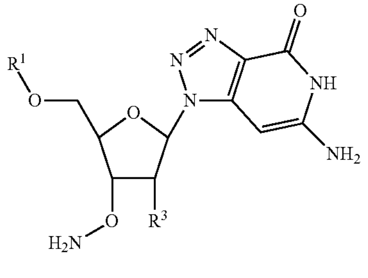

(b)

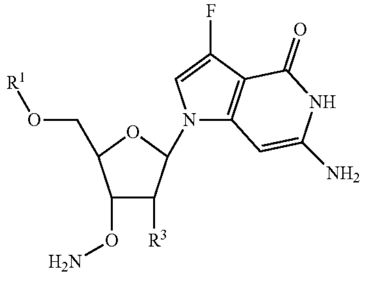

-continued
(c)
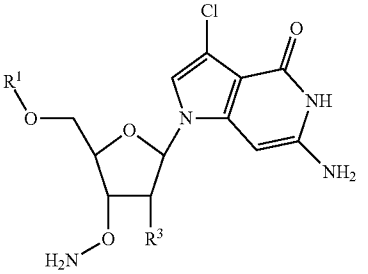
(d)
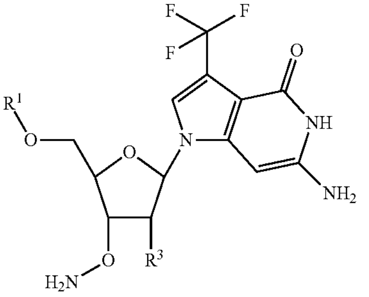
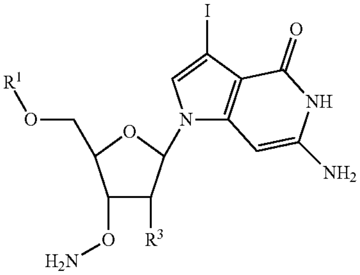
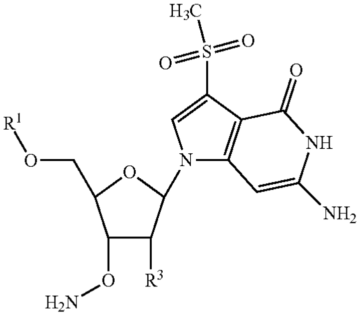
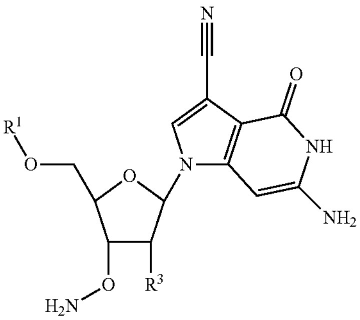
-continued
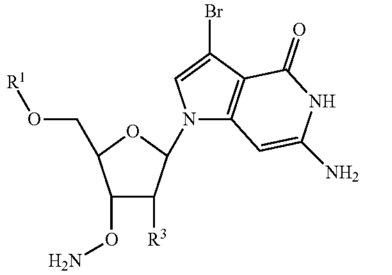
wherein, $R^1$ is a phosphate or polyphosphate group or salt thereof, optionally containing one or more sulfur atoms.
The compounds of Formula (1a) or (1b) can also be selected from the group consisting of:
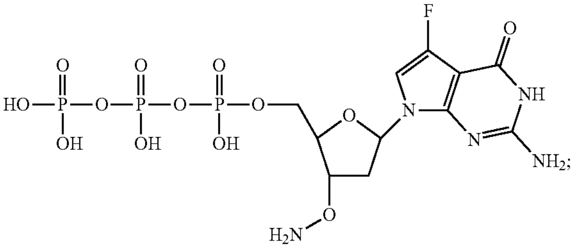
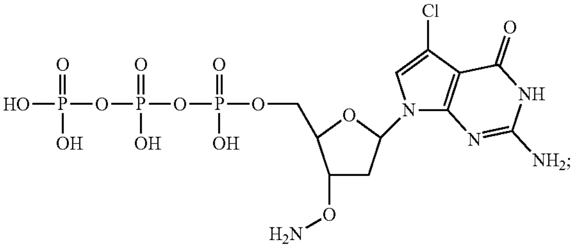
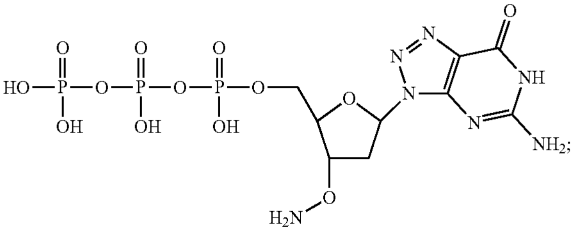
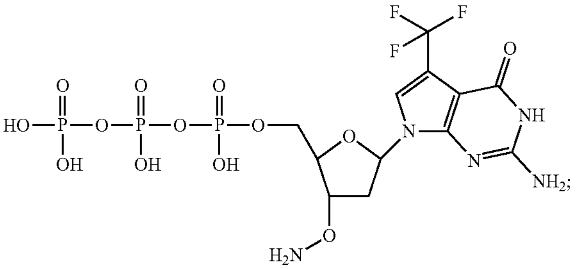

-continued
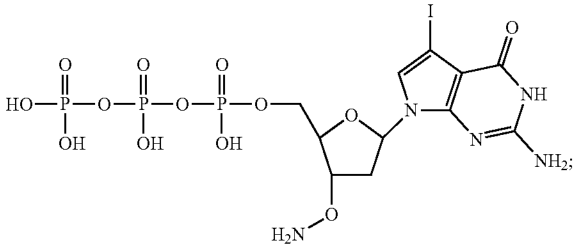
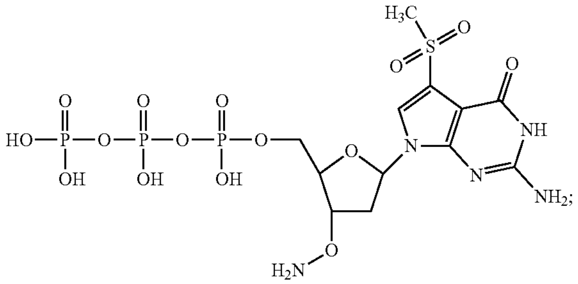
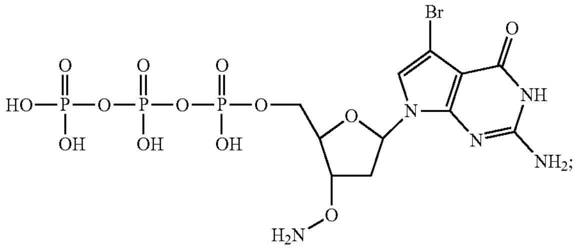
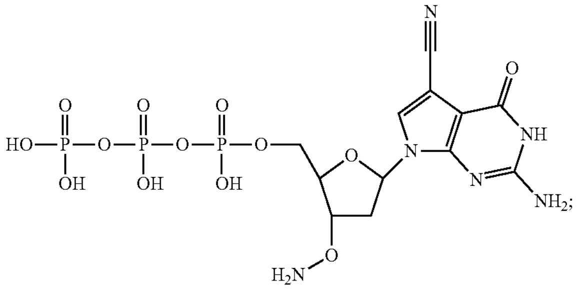
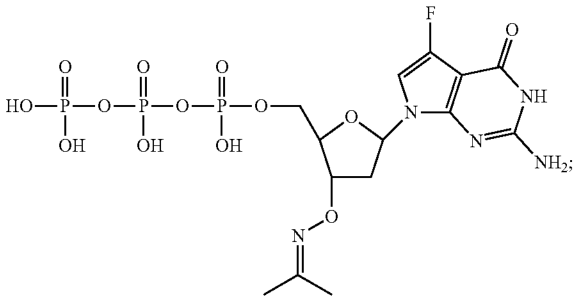
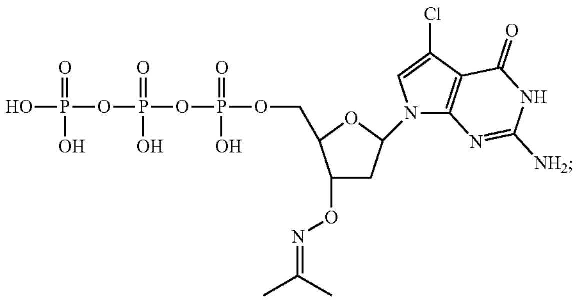
-continued
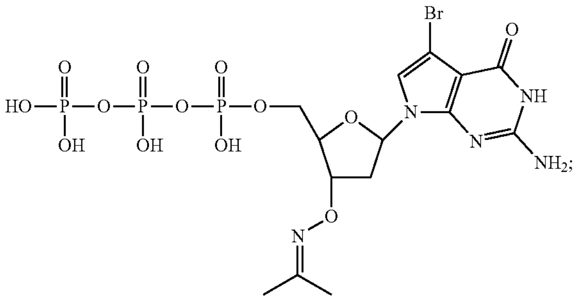
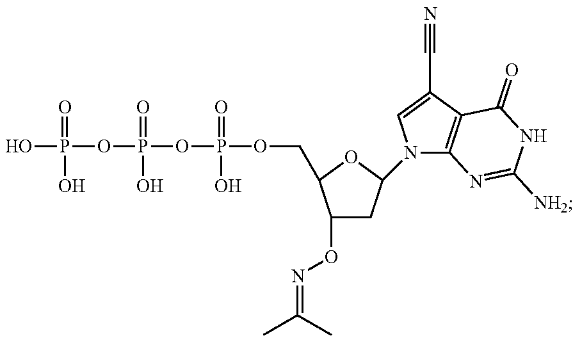
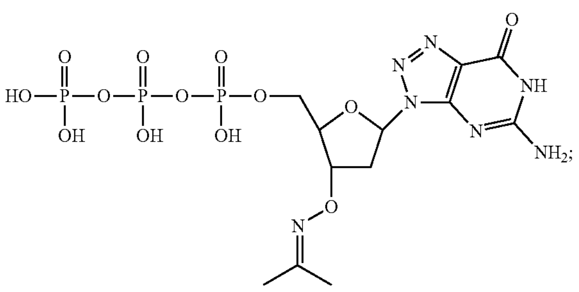
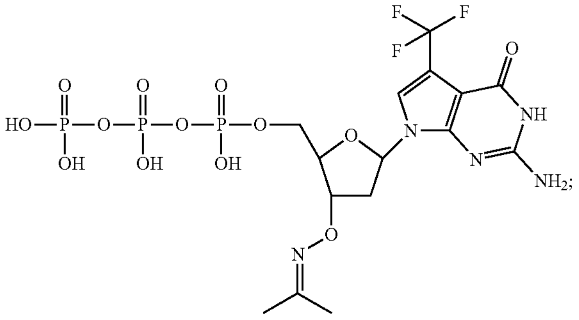
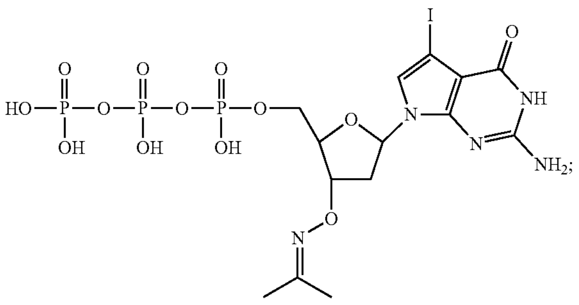

-continued

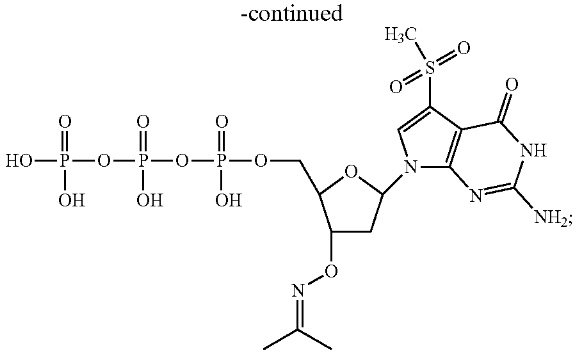

or a salt thereof.

Included herein is a method of nucleic acid synthesis comprising reacting a compound of Formula (1a) or (1b) with an oligonucleotide in the presence of a polymerase or terminal deoxynucleotidyl transferase (TdT) enzyme and treating the extended oligonucleotide with a nitrite salt.

The terminal transferase or modified terminal transferase can be any enzyme capable of template independent strand extension. The modified terminal deoxynucleotidyl transferase (TdT) enzyme can comprise amino acid modifications when compared to a wild type sequence or a truncated version thereof. The terminal transferase can be the homologous amino acid sequence of a terminal deoxynucleotidyl transferase (TdT) enzyme in any species or the homologous amino acid sequence of Polμ, Polβ, Polλ, and Polθ of any species or the homologous amino acid sequence of X family polymerases of any species.

Homologous refers to protein sequences between two or more proteins that possess a common evolutionary origin, including proteins from superfamilies in the same species of organism as well as homologous proteins from different species. Such proteins (and their encoding nucleic acids) have sequence homology, as reflected by their sequence similarity, whether in terms of percent identity or by the presence of specific residues or motifs and conserved positions. A variety of protein (and their encoding nucleic acid) sequence alignment tools may be used to determine sequence homology. For example, the Clustal Omega multiple sequence alignment program provided by the European Molecular Biology Laboratory (EMBL) can be used to determine sequence homology or homologous regions.

A further embodiment of the present invention relates to the oligonucleotide sequence comprising a solid-supported oligonucleotide sequence. The oligonucleotide sequence comprises 2 or more nucleotides. The oligonucleotide sequence can be between 10 and 500 nucleotides, such as between 20 and 200 nucleotides, in particular between 20 and 50 nucleotides long.

A further embodiment of the present invention relates to a method further comprising a reaction step with a nitrite salt. Preferably, the nitrate salt is sodium nitrite.

A further aspect of the present invention relates to a kit comprising:

(i) a compound according to any one of Formula (1a) or (1b);

(ii) a polymerase or terminal deoxynucleotidyl transferase (TdT) enzyme; and optionally (iii) a nitrite salt.

A further aspect of the present invention relates to an oligonucleotide according to Formula (1a) or (1b) or (2a) or (2b).

A further embodiment of the present invention relates to an oligonucleotide according to Formula (2a) or (2b) wherein $R^1$ can be an oligonucleotide. The phosphates in $R^1$ can contain one or more sulfur atoms.

A further embodiment of the present invention relates to a compound according to Formula (1a) or (1b) or (2a) or (2b) wherein $R^2$ can be an electron withdrawing group (EWG). $R^2$ can be an electron withdrawing group (EWG) that can be selected from the group consisting of halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$. $R^2$ can be an electron withdrawing group (EWG) consisting of a halo group. $R^2$ can be an electron withdrawing group (EWG) consisting of a halo group which can be selected from F, Cl, Br or I. $R^2$ can be F or Cl. $R^2$ can be an electron withdrawing group (EWG) consisting of a nitrile group. $R^2$ can be an electron withdrawing group (EWG) consisting of a halomethyl group. $R^2$ can be an electron withdrawing group (EWG) consisting of a dihalomethyl group. $R^2$ can be an electron withdrawing group (EWG) consisting of a trihalomethyl group. $R^2$ can be an electron withdrawing group (EWG) consisting of a $C{\equiv}CR^4$ group. $R^2$ can be an electron withdrawing group (EWG) consisting of a $SOR^4$ group. $R^2$ can be an electron withdrawing group (EWG) consisting of a $SO_2R^4$ group. $R^2$ can be an electron withdrawing group (EWG) consisting of a $SO_2CH_3$ group. $R^2$ can be an electron withdrawing group (EWG) consisting of a $COR^4$ group. $R^2$ can be an electron withdrawing group (EWG) consisting of a $CO_2R^4$ group. $R^2$ can be an electron withdrawing group (EWG) consisting of a $CONR^4R^5$ group.

A further embodiment of the present invention relates to an oligonucleotide according to Formula (1a) or (1b) or (2a) or (2b) wherein $R^3$ can be selected from H, OH, F, $OCH_3$, or $OCH_2CH_2OMe$. $R^3$ can be OH. $R^3$ can be F. $R^3$ can be $OCH_3$. $R^3$ can be $OCH_2CH_2OMe$. Preferably, $R^3$ can be H.

A further embodiment of the present invention relates to a compound according to Formula (2a) or (2b) wherein $R^4$ can be independently selected from H and $C_{1-6}$ alkyl optionally substituted with OH or halo atoms. $R^4$ can be H. $R^4$ can be $C_{1-6}$ alkyl optionally substituted with OH or halo atoms, wherein the halo atoms can be selected from F, Cl, Br or I. $R^4$ can be $C_{1-6}$ alkyl optionally substituted with OH or 1-6 halo atoms, wherein the halo atoms can be selected from F, Cl, Br or I.

A further embodiment of the present invention relates to a compound according to Formula (2a) or (2b) wherein $R^5$ can be independently selected from H and $C_{1-6}$ alkyl optionally substituted with OH or halo atoms. $R^5$ can be H. $R^5$ can be $C_{1-6}$ alkyl optionally substituted with OH or halo atoms, wherein the halo atoms can be selected from F, Cl, Br or I. $R^5$ can be $C_{1-6}$ alkyl optionally substituted with OH or 1-6 halo atoms, wherein the halo atoms can be selected from F, Cl, Br or I.

Described herein is a process of nucleic acid synthesis using the compounds described herein. The process uses a nucleic acid polymerase, which may be a template independent polymerase or a template dependent polymerase to add a single nucleotide to one or more nucleic acid strands. The strands may be immobilised on a solid support. The process involves cleaving the 3'-aminooxy group and adding a further nucleotide, the base of which may or may not be G.

Disclosed is a method of nucleic acid synthesis comprising reacting a compound described herein with an oligonucleotide in the presence of a polymerase or terminal deoxynucleotidyl transferase (TdT) enzyme and treating the extended oligonucleotide with a nitrite salt.

In the methods of nucleic acid synthesis described herein the oligonucleotide sequence may be a solid-supported oligonucleotide sequence.

In the methods of nucleic acid synthesis described herein the nitrite salt may be sodium nitrite. Disclosed is a method of nucleic acid synthesis comprising:

(a) providing an initiator sequence;

(b) adding extension reagents comprising a polymerase or terminal deoxynucleotidyl transferase (TdT) and a compounds according to Formula (1a) or (1b):

(1a)

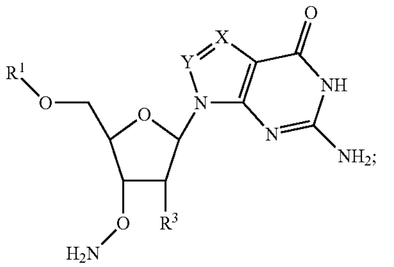

(1b)

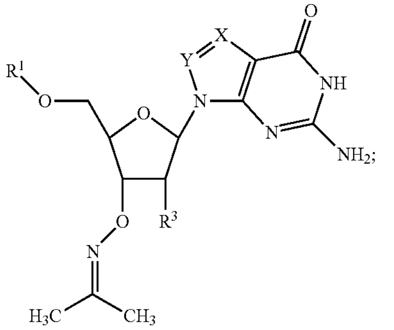

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either

X is N and Y is N, or X is $CR^2$ and Y is CH or N, where $R^2$ is an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms, and (c) optionally transforming the $N{=}C(CH_3)_2$ if present to $NH_2$;

(d) converting the 3'-O—$NH_2$ group on the extended nucleic acid polymer to a 3'-OH group;

(e) adding extension reagents comprising a 3'-O—$NH_2$ or 3'-O—$N{=}C(CH_3)_2$ blocked nucleoside triphosphate and a polymerase or terminal deoxynucleotidyl transferase (TdT) to said initiator sequence to add a further single nucleotide to the initiator sequence.

The nucleic acids synthesised can be any sequence. One or more, possibly all, of the guanine bases will have the electron withdrawing group at the 7- or 8-position. A population of different sequences can be synthesised in parallel.

Where the cytosine or adenine heterocyclic bases have exocyclic $NH_2$ groups, these groups can optionally be masked by an orthogonal masking agent. The amine masked nitrogenous heterocycles may be N4-amine masked cytidine and N6-amine masked adenine. The masking may be for example an azido ($N_3$) group. Example for suitable masking groups include azide (—$N_3$), benzoylamine (N-benzoyl or —NHCOPh), N-methyl (—NHMe), isobutyrylamine, dimethylformamidylamine, 9-fluorenylmethyl carbamate, t-butyl carbamate, benzyl carbamate, acetamide (N-acetyl or —NHCOMe), trifluoroacetamide, pthlamide, benzylamine (N-benzyl or —NH—$CH_2$-phenyl), triphenylmethylamine, benxylideneamine, tosylamide, isothiocyanate, N-allyl (such as N-dimethylallyl (—$NHCH_2$—$CH{=}CH_2$)) and N-anisoyl (—NHCOPh-OMe), such as azide (—$N_3$), N-acetyl (—NHCOMe), N-benzyl (—NH—$CH_2$-phenyl), N-anisoyl (—NHCOPh-OMe), N-methyl, (—NHMe), N-benzoyl (—NHCOPh), N-dimethylallyl (—$NHCH_2$—$CH{=}CH_2$).

References herein to an "amine masking group" refer to any chemical group which is capable of generating or "unmasking" an amine group which is involved in hydrogen bond base-pairing with a complementary base. Most typically the unmasking will follow a chemical reaction, most suitably a simple, single step chemical reaction. The amine masking group will generally be orthogonal to the 3'-O—$NH_2$ blocking group in order to allow selective removal.

In the nucleic acids synthesised, the bases can be selected from: T or modified T such as for example 'super-T'; C or a modified C such as for example a C having an electron withdrawing group at the 5 position, as described herein; A or a modified A such as for example an N6-amine masked adenine; and G or a modified G such as for example an N2-amine masked guanine. The amino masking group prevents de-amination caused by the nitrite exposure needed to remove the O—$NH_2$ at the 3'-position of the sugar.

The T nucleotides can be selected from (1a)

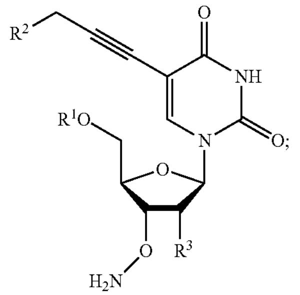

(1b)

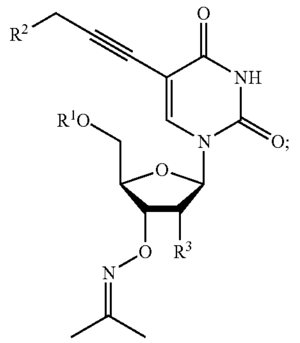

wherein, $R^1$ is a phosphate or polyphosphate group or salt thereof, optionally containing one or more sulfur atoms;

$R^2$ is H, halo, OH, $NH_2$, COOH, COH, $C_{1-3}$ alkoxy, $C_{1-3}$ alkyl optionally substituted with OH, $NH_2$ or halo atoms; and $R^3$ is selected from H, OH, F, $OCH_3$ or $OCH_2CH_2OMe$.

The T nucleotides can be

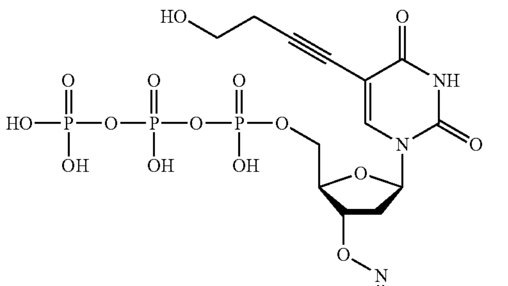

or

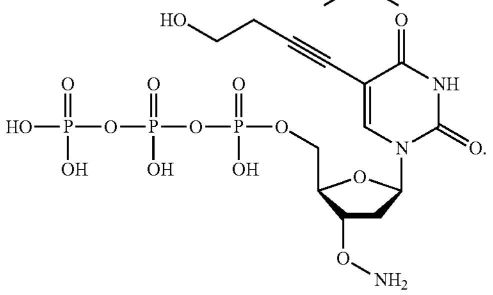

or a salt thereof.

The adenine compounds may be selected from:

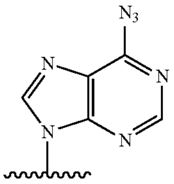 [SMILES: *n1cnc2c(N=[N+]=[N-])ncnc21]

The term 'azide' or 'azido' used herein refers to an —$N_3$, or more specifically, an —N═$N^+$═$N^-$ group. It will also be appreciated that azide extends to the presence of a tetrazolyl moiety. The "azide-tetrazole" equilibrium is well known to the skilled person from Lakshman et al (2010) J. Org. Chem. 75, 2461-2473. Thus, references herein to azide extend equally to tetrazole as illustrated below when applied to the $R^3$ groups defined herein:

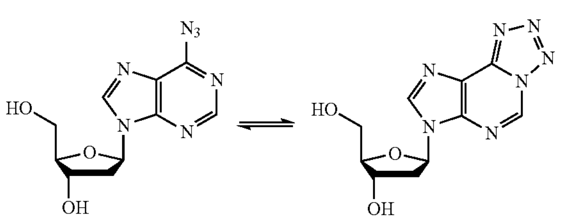

This embodiment has the advantage of reversibly masking the —$NH_2$ group. While blocked in the —$N_3$ state, the base (B) is impervious to deamination (e.g., deamination in the presence of sodium nitrite). The base (B) in the N-blocked form is incapable of forming secondary structures via base pairing. Thus, even blocking a subset of the free amino groups in the nucleic acid polymer improves the availability of the 3'-end for further extension. The canonical adenine can be respectively recovered from 2-azido guanine by exposure to a reducing agent (e.g., TCEP). Thus, the —$N_3$ group serves as an effective protecting group against deamination, especially in the presence of sodium nitrite.

Alternatively the A bases may be modified at the 7 or 8 positions in a similar manner to the modifications described herein. The A bases may also be modified at the 2 position. The A nucleoside may be of formula:

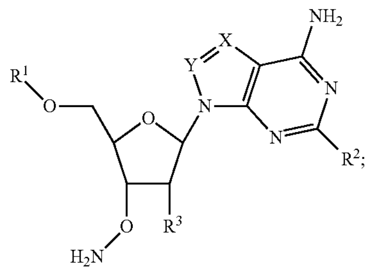

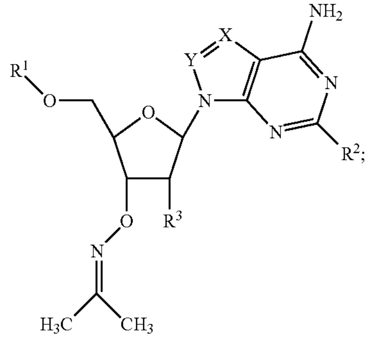

wherein, $R^1$ is a phosphate or polyphosphate group or salt thereof, optionally containing one or more sulfur atoms;

$R^2$ is H or an electron withdrawing group (EWG) selected from the group consisting of: halo; nitro, nitrosyl, nitrile; halomethyl, dihalomethyl, trihalomethyl; C≡$CR^4$; $SOR^4$; $SO_2R^4$; $SO_3R^4$; $COR^4$; $CO_2R^4$; $CONR^4R^5$;

$R^3$ is selected from H, OH, F, $OCH_3$, or $OCH_2CH_2OMe$; and

X is N, CH, $CR^7$ where $R^7$ is optionally substituted $C_{1-5}$ alkyl, optionally substituted $C_{1-5}$ alkenyl or optionally substituted $C_{1-5}$ alkynyl, or $CR^8$ where $R^8$ is an electron withdrawing group (EWG) selected from the group consisting of: halo; nitro, nitrosyl, nitrile; halomethyl, dihalomethyl, trihalomethyl; C≡$CR^4$; $SOR^4$; $SO_2R^4$; $SO_3R^4$; $COR^4$; $CO_2R^4$; $CONR^4R^5$; and Y is CH or N; and either X is N and Y is N, or X is $CR^8$ where $R^8$ is an electron withdrawing group (EWG) selected from the group consisting of: halo; nitro, nitrosyl, nitrile; halomethyl, dihalomethyl, trihalomethyl; C≡$CR^4$; $SOR^4$; $SO_2R^4$; $SO_3R^4$; $COR^4$; $CO_2R^4$; $CONR^4R^5$, and/or $R^2$ is H or an electron withdrawing group (EWG) selected from the group consisting of: halo; nitro, nitrosyl, nitrile; halomethyl, dihalomethyl, trihalomethyl; $C{\equiv}CR^4$; $SOR^4$; $SO_2R^4$; $SO_3R^4$; $COR^4$; $CO_2R^4$; $CONR^4R^5$;

wherein each $R^4$ and $R^5$ are independently selected from H and $C_{1-6}$ alkyl optionally substituted with OH or halo atoms.

It will be appreciated that the compounds of the invention may be readily applied to methods of enzymatic nucleic acid synthesis which are well known to the person skilled in the art. Non-limiting methods of nucleic acid synthesis may be found in WO 2016/128731, WO 2016/139477, WO 2017/009663, GB 1613185.6 and GB 1714827.1, the contents of each of which are herein incorporated by reference.

Enzymatic nucleic acid synthesis is defined as any process in which a nucleotide is added to a nucleic acid strand through enzymatic catalysis in the presence or absence of a template. For example, a method of enzymatic nucleic acid synthesis could include non-templated de novo nucleic acid synthesis utilizing a PolX family polymerase, such as terminal deoxynucleotidyl transferase, and reversibly terminated 2'-deoxynucleoside 5'-triphosphates or ribonucleoside 5'-triphosphate. Another method of enzymatic nucleic acid synthesis could include templated nucleic acid synthesis, including sequencing-by-synthesis. Reversibly terminated enzymatic nucleic acid synthesis is defined as any process in which a reversibly terminated nucleotide is added to a nucleic acid strand through enzymatic catalysis in the presence or absence of a template. Thus, in one embodiment, the method of enzymatic nucleic acid synthesis is selected from a method of reversibly terminated enzymatic nucleic acid synthesis and a method of templated and non-templated de novo enzymatic nucleic acid synthesis. References herein to 'nucleoside triphosphates' refer to a molecule containing a nucleoside (i.e. a base attached to a deoxyribose or ribose sugar molecule) bound to three phosphate groups. Examples of nucleoside triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of nucleoside triphosphates that contain ribose are: adenosine triphosphate (ATP), guanosine triphosphate (GTP), cytidine triphosphate (CTP) or uridine triphosphate (UTP). Other types of nucleosides may be bound to three phosphates to form nucleoside triphosphates, such as naturally occurring modified nucleosides and artificial/modified/non-naturally occurring nucleosides.

Therefore, references herein to '3'-blocked nucleoside triphosphates' refer to nucleoside triphosphates (e.g., dATP, dGTP, dCTP or dTTP) which have an additional group on the 3'-end which prevents further addition of nucleotides, i.e., by replacing the 3'-OH group with a protecting group. Herein the protecting group is $NH_2$ or a protected version thereof.

References herein to a 'DNA initiator sequence' refer to a small sequence of DNA which the 3'-blocked nucleoside triphosphate can be attached to, i.e., DNA will be synthesised from the 3'-end of the DNA initiator sequence.

In one embodiment, the initiator sequence is between 5 and 100 nucleotides long, such as between 10 and 60 nucleotides long, in particular between 20 and 50 nucleotides long. The ideal length of initiator may be informed by the immobilisation state (i.e. in solution or immobilised), the immobilisation chemistry, the initiator base sequence, and other parameters.

In one embodiment, the initiator sequence is single-stranded. In an alternative embodiment, the initiator sequence is double-stranded. In a further embodiment, the initiator sequence has double-stranded and single-stranded portions. It will be understood by persons skilled in the art that a 3'-overhang (i.e., a free 3'-end) allows for efficient addition.

In one embodiment, the initiator sequence is immobilised on a solid support. This allows the enzyme and the cleaving agent to be removed without washing away the synthesised nucleic acid. The initiator sequence may be attached to a solid support stable under aqueous conditions so that the method can be easily performed via a flow setup.

In one embodiment, the initiator sequence is immobilised on a solid support via a reversible interacting moiety, such as a chemically-cleavable linker, an antibody/immunogenic epitope, a biotin/biotin binding protein (such as avidin or streptavidin), or glutathione-GST tag. Therefore, in a further embodiment, the method additionally comprises extracting the resultant nucleic acid by removing the reversible interacting moiety in the initiator sequence, such as by incubating with proteinase K.

In one embodiment, the initiator sequence contains a base or base sequence recognisable by an enzyme. A base recognised by an enzyme, such as a glycosylase, may be removed to generate an abasic site which may be cleaved by chemical or enzymatic means. An example of such a glycosylase system includes the presence of a uracil base in the initiator sequence, which may be excised with uracil DNA glycosylase (UDG) to leave an abasic site which may be cleaved with, for example, basic solutions, organic amines, or an endonuclease (such as endonuclease VIII), to release a nucleic acid bearing a 5'-phosphate into solution. A base sequence may be recognised and cleaved by a restriction enzyme.

In a further embodiment, the initiator sequence is immobilised on a solid support via an orthogonal chemically-cleavable linker, such as a disulfide, allyl, or azide-masked hemiaminal ether linker. Therefore, in one embodiment, where an azido N-masking group is not present, the method additionally comprises extracting the resultant nucleic acid by cleaving the chemical linker through the addition of tris(2-carboxyethyl)phosphine (TCEP) or dithiothreitol (DTT) for a disulfide linker; palladium complexes or an allyl linker; or TCEP for an azide-masked hemiaminal ether linker.

In one embodiment, the resultant nucleic acid is extracted and amplified by polymerase chain reaction (PCR) using the nucleic acid bound to the solid support as a template. The initiator sequence could therefore contain an appropriate forward primer sequence and an appropriate reverse primer could be synthesised or incorporated via ligation.

In one embodiment, the terminal deoxynucleotidyl transferase (TdT) of the invention is added in the presence of an extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc. all with appropriate counterions, such as Cl) and inorganic pyrophosphatase (e.g., the *Saccharomyces cerevisiae* homolog). It will be understood that the choice of buffers and salts depends on the optimal enzyme activity and stability. The use of an inorganic pyrophosphatase helps to reduce the build-up of pyrophosphate due to nucleoside triphosphate hydrolysis by TdT. Therefore, the use of an inorganic pyrophosphatase has the advantage of reducing the rate of (1) backwards reaction and (2) TdT strand dismutation.

In one embodiment, step (b) is performed at a pH range between 5 and 10. Therefore, it will be understood that any buffer with a buffering range of pH 5-10 could be used, for example cacodylate, Tris, HEPES or Tricine, in particular cacodylate or Tris.

The compounds of the invention can be used on a device for nucleic acid synthesis. In one embodiment of the invention there is a solid support in the form of for example a planar array and further a plurality of beads onto which a plurality of immobilized initiation oligonucleotide sequences are attached. The beads may be porous and a portion of the, optionally porous, beads are selected as anchors and unselected beads are exposed to harvest solution to cleave them from their solid support to release the oligonucleotide sequences into solution. Thus the term solid support can refer to an array having a plurality of beads which may or may not be immobilised. The oligonucleotides may be attached to, or removed from beads whilst on the array. Thus the immobilised oligonucleotide may be attached to a bead, which remains in a fixed position on the array whilst other beads in other locations are subject to cleavage conditions to detach the oligonucleotides from the beads (the beads may or may not be immobilised).

The solid support can take the form of a digital microfluidic device. Digital microfluidic devices consist of a plurality of electrodes arranged on a surface. A dielectric layer (e.g., aluminum oxide) is deposited over the electrodes followed by a hydrophobic coating (e.g., perfluorinated hydrocarbon polymer) atop the dielectric layer. The electrodes may be hardwired or formed from an active matrix thin film transistor (AM-TFT).

The solid support can take the form of a digital microfluidic device. Digital microfluidic devices consist of a plurality of electrodes arranged on a surface. These electrodes can be addressed in a passive manner or by active matrix methods. Passive addressing is a direct address where actuation signals are directly applied on individual electrode (for example by means of a hard-wired connection to that electrode in a single layer or multilayer fashion such as a printed circuit board, PCB). However, a limitation of direct drive methods is the inability to process large numbers of droplets due to difficulties in addressing large numbers of direct drive electrodes. In active matrix addressing, M×N electrodes can be controlled by M+N pins, significantly reducing the number of control pins. However, the resolution of the electrodes (size of electrodes as compared to the size of droplets) limits the scope of droplet operations. Active matrix thin film transistor (AM-TFT) technology enables the control of large numbers of droplets by replacing patterned electrodes with a thin film transistor array, each of which is individually addressable. The increased resolution (small size of pixels on the thin film transistor array) also increases the scope of droplet operations. An AM-TFT digital microfluidic device comprises a dielectric layer (e.g., aluminum oxide) deposited over the electrode layer on the thin-film transistor layer followed by a hydrophobic coating (e.g., perfluorinated hydrocarbon polymer) atop the dielectric layer.

Depending on applied voltage to a subset of the plurality of electrodes arranged on the aforementioned surface, aqueous droplets may be actuated across the surface immersed in oil, air, or another fluid. Enzymatic oligonucleotide synthesis can be deployed on a digital microfluidic device in several ways. An initiator oligonucleotide can be immobilized via the 5'-end on super paramagnetic beads or directly to the hydrophobic surface of the digital microfluidic device. A plurality of distinct positions containing immobilized initiator oligonucleotides on the digital microfluidic device may be present (henceforth named synthesis zones). Solutions required for enzymatic oligonucleotide synthesis are then dispensed from multiple reservoirs onto the device. Briefly, an addition solution containing the components necessary for the TdT-mediated incorporation of reversibly terminated nucleoside 5'-triphosphates onto immobilized initiator oligonucleotides can be dispensed from a reservoir in droplets and actuated to the aforementioned positions containing immobilized initiator oligonucleotides. During this stage, each reservoir (and thus each droplet containing addition solution) can contain a distinct nitrogenous base reversibly terminated nucleoside 5'-triphosphate identity or a mixture thereof in order to control the sequence synthesized on aforementioned positions containing immobilized initiator oligonucleotides.

Alternatively the method can be implemented on continuous flow microfluidic devices. One such device consists of a surface with a plurality of microwells each containing a bead. On said bead, an oligonucleotide initiator can be immobilized. In addition to each microwell containing a bead with immobilized initiator, each microwell can contain an electrode to perform electrochemistry. Another implementation of continuous flow microfluidics consists of a fritted column containing beads or resin on which initiator sequences are immobilized. Addition, wash, and deblocking solutions may be sequentially flowed through the column in a process of DNA synthesis.

In all examples of nucleic acid synthesis, the use of the modified bases having the electron withdrawing groups improves the quality of the synthesised strands due to lowering the level of deamination.

(a). BzCl, pyridine; (b). N-Iodosuccinimide, DMF; (c) $TMSCF_3$, CuI, KF, DMF/NMP; (d). NaOMe, MeOH; (e). TMSCl, NaI, MeCN.

Figure 1:
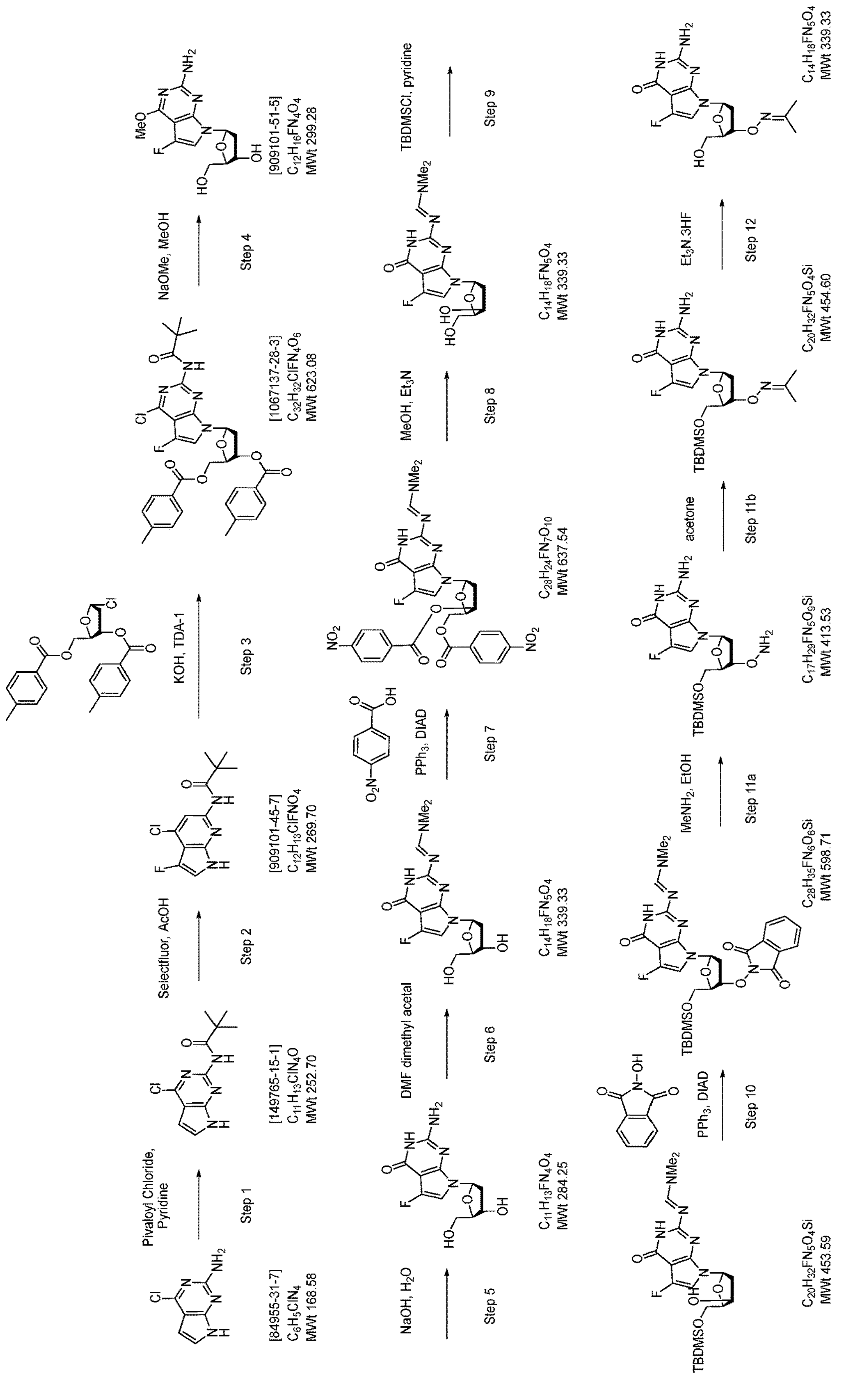
FIG. 1: Synthetic route to 7-deaza-7-F-dG reversible terminator.
Figure 2:
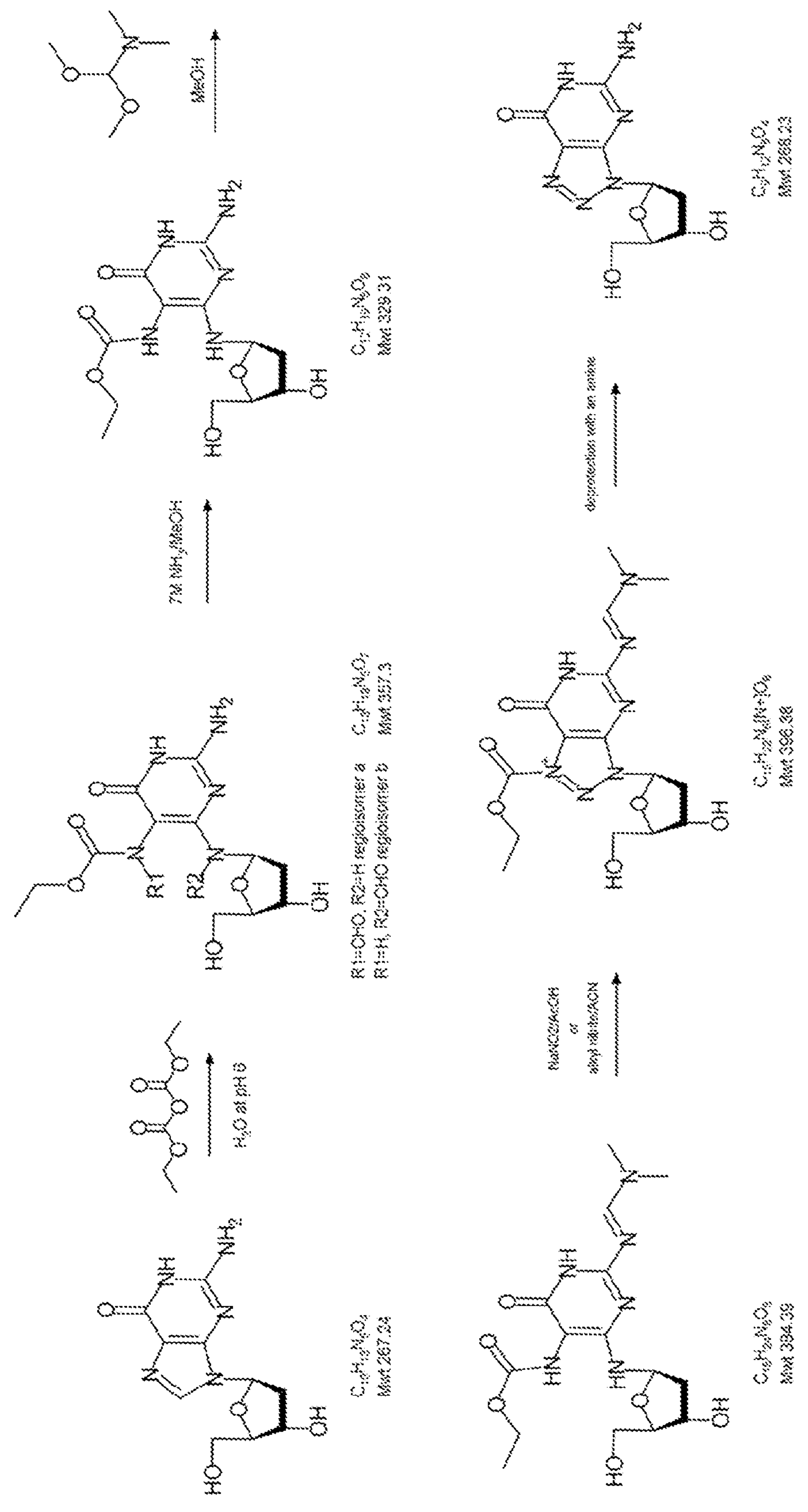
FIG. 2: Synthetic route to 8-aza-dG reversible terminator.
Figure 3:
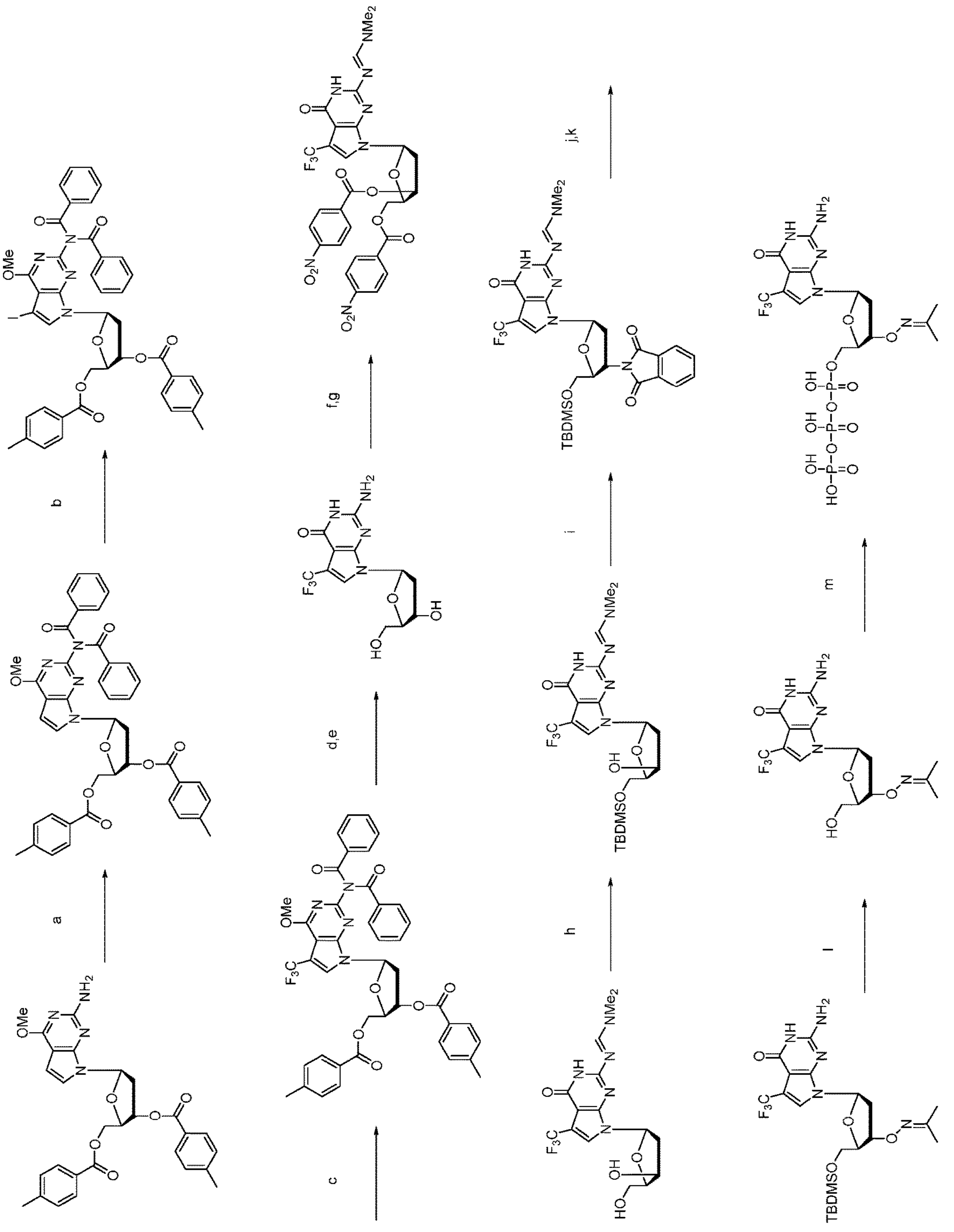
FIG. 3: Synthetic route to 7-Deaza-7-Trifluoromethyl-dG Reversible Terminator Triphosphate.
Figure 4:
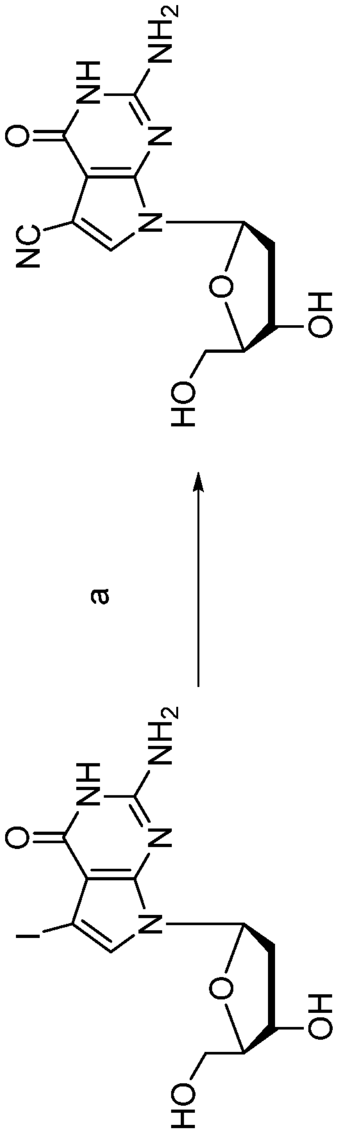

FIG. 4: Synthetic route to 7-Deaza-7-cyano-2'-deoxyguanosine.

(a). CuCN, Pyridine, 100° C.

Figure 5:
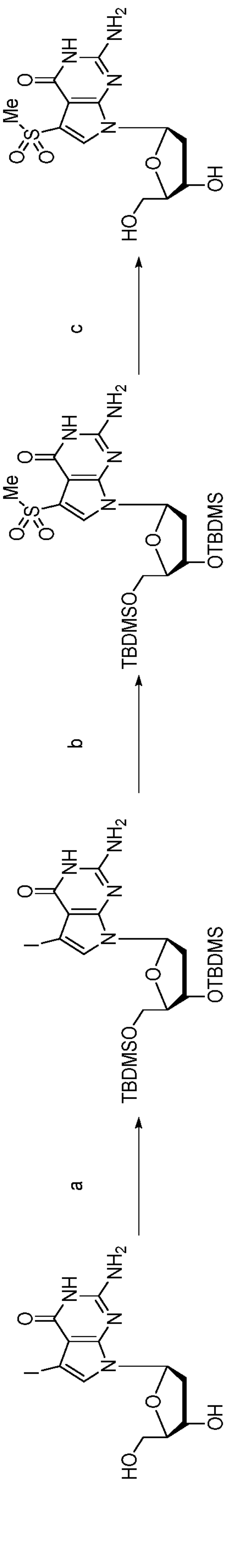

FIG. 5: Synthetic route to 7-Deaza-7-methanesulfonyl-2'-deoxyguanosine.

(a). TBDMSCl, pyridine; (b). $MeSO_2Na$, CuI, DMF; (c) $3HF \cdot Et_3N$, THF.

Figure 6:
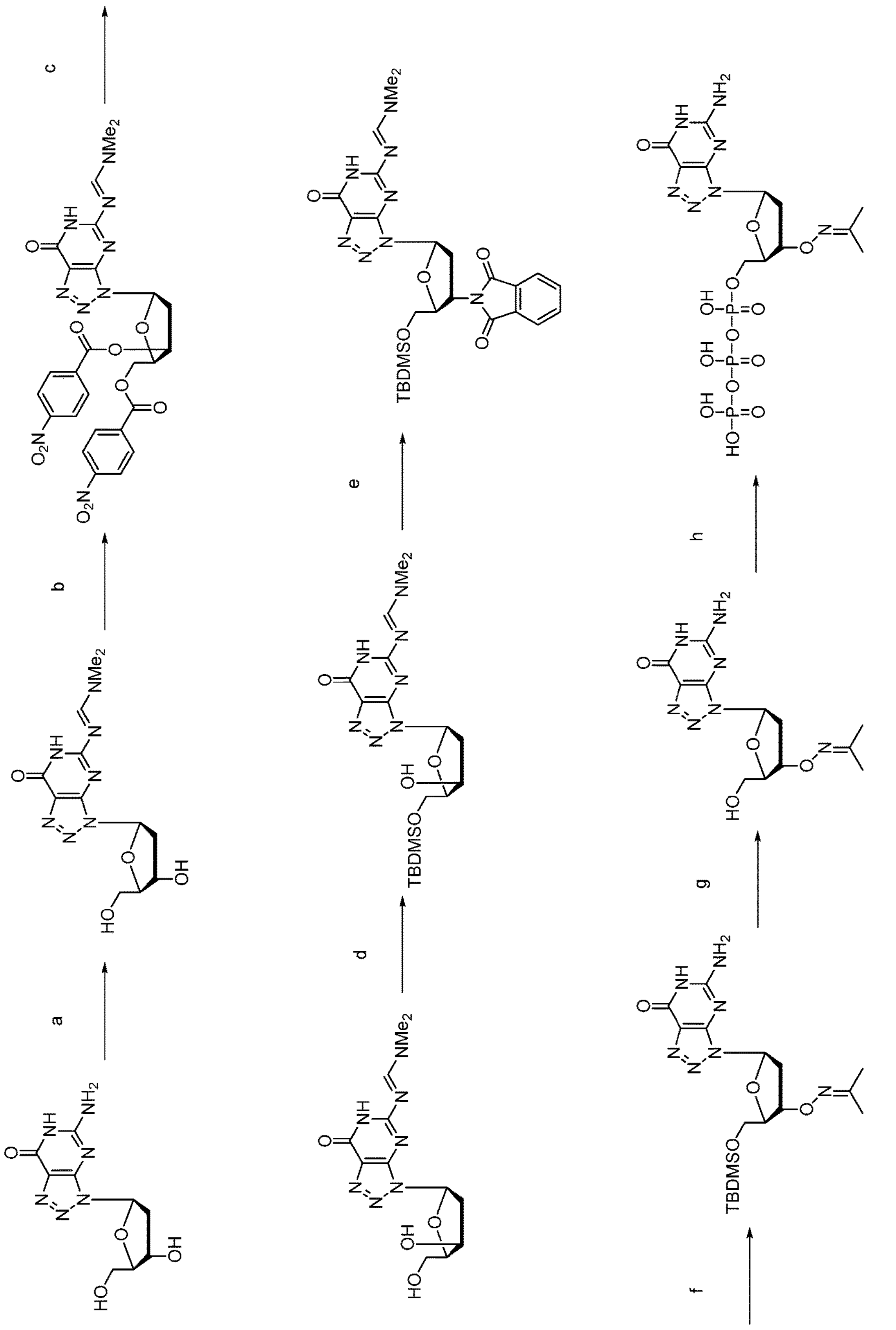

FIG. 6: Synthetic route to 3'-(O)-Acetoxime-8-aza-2'-deoxyguanosine triphosphate.

(a). DMF dimethyl acetal; (b). 4-Nitrobenzoic acid, $PPh_3$, DIAD, THF; (c). MeOH. $Et_3N$; (d). TBDMSCl, pyridine, DMF; (e). N-Hydroxyphthalimide, $PPh_3$, DIAD, THF; (f). i. $MeNH_2$, EtOH; ii. acetone; (g). $3HF \cdot Et_3N$, THF; (h). i. 2-Chloro-1,3,2-benzodioxaphosphorin-4-one, pyridine, dioxane; ii. $Bu_3N \cdot H_4P_2O_7$, DMF; iii. $I_2$; iv. $H_2O$.

Figure 7:
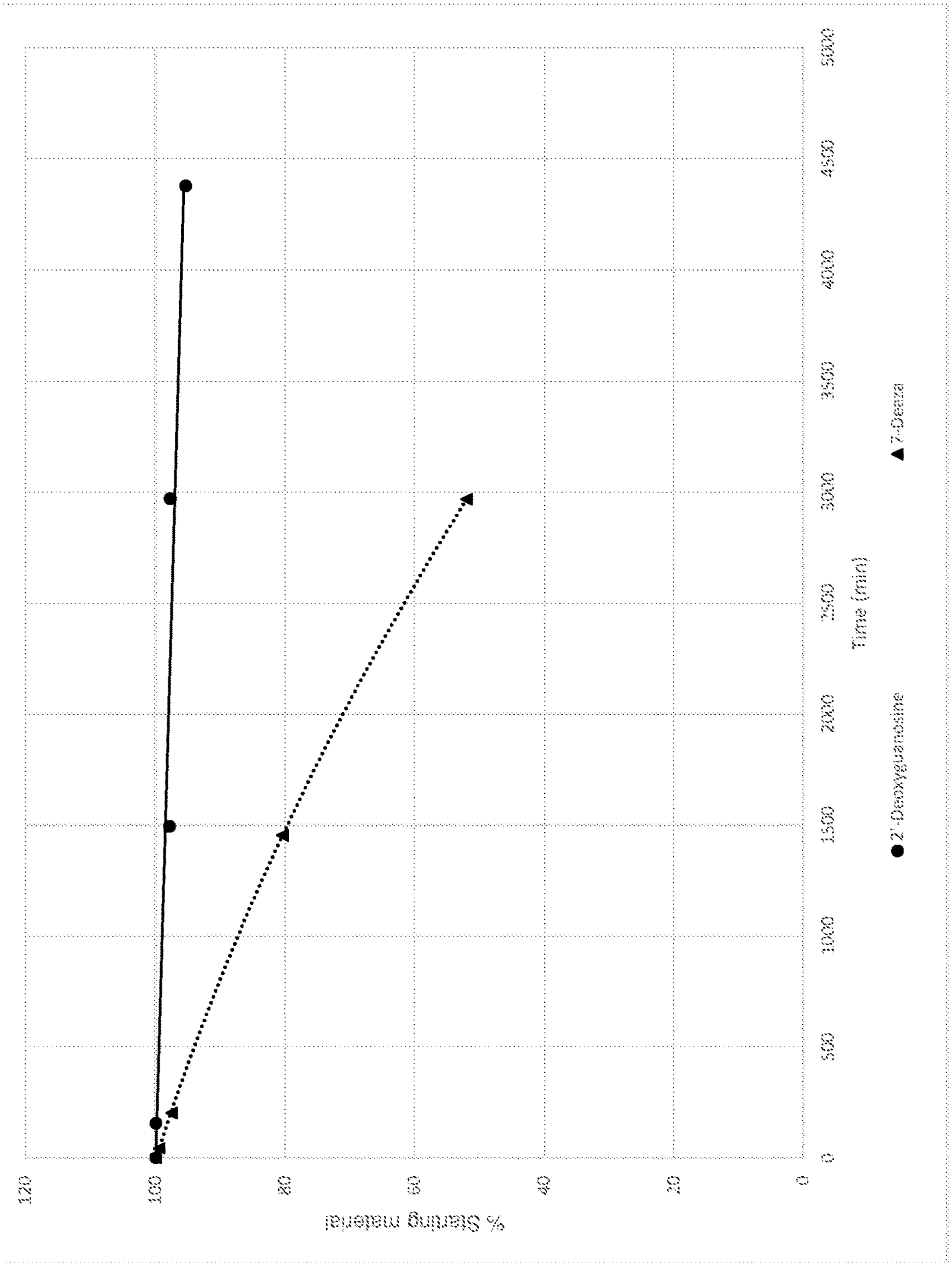

FIG. 7: Graph showing the stability of dG and 7-Deaza-dG in NDS at room temperature.

Figure 8:
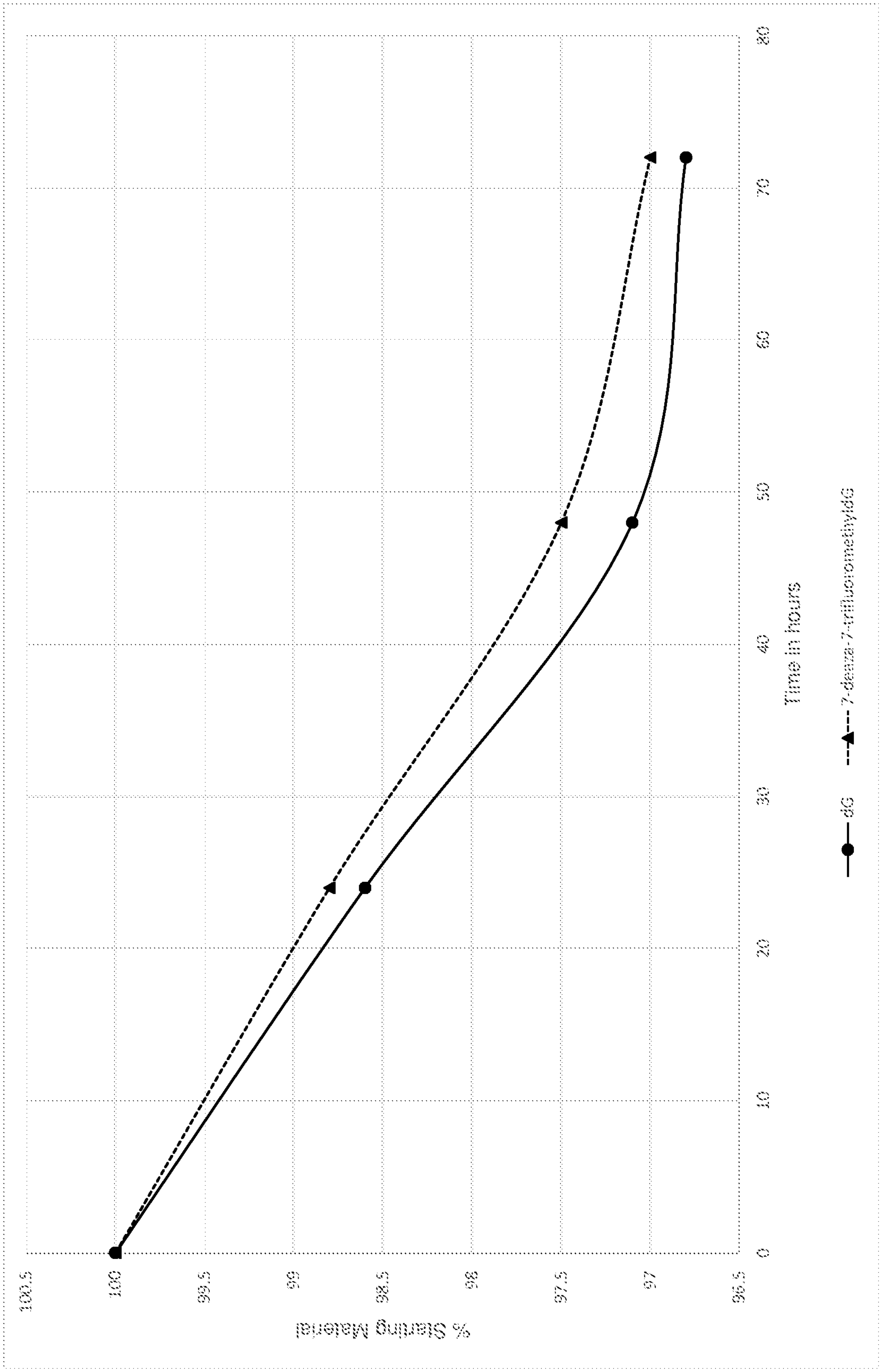

FIG. 8: Graph showing the stability of dG and 7-Deaza-7-Trifluoromethyl-dG in NDS.

Figure 9:
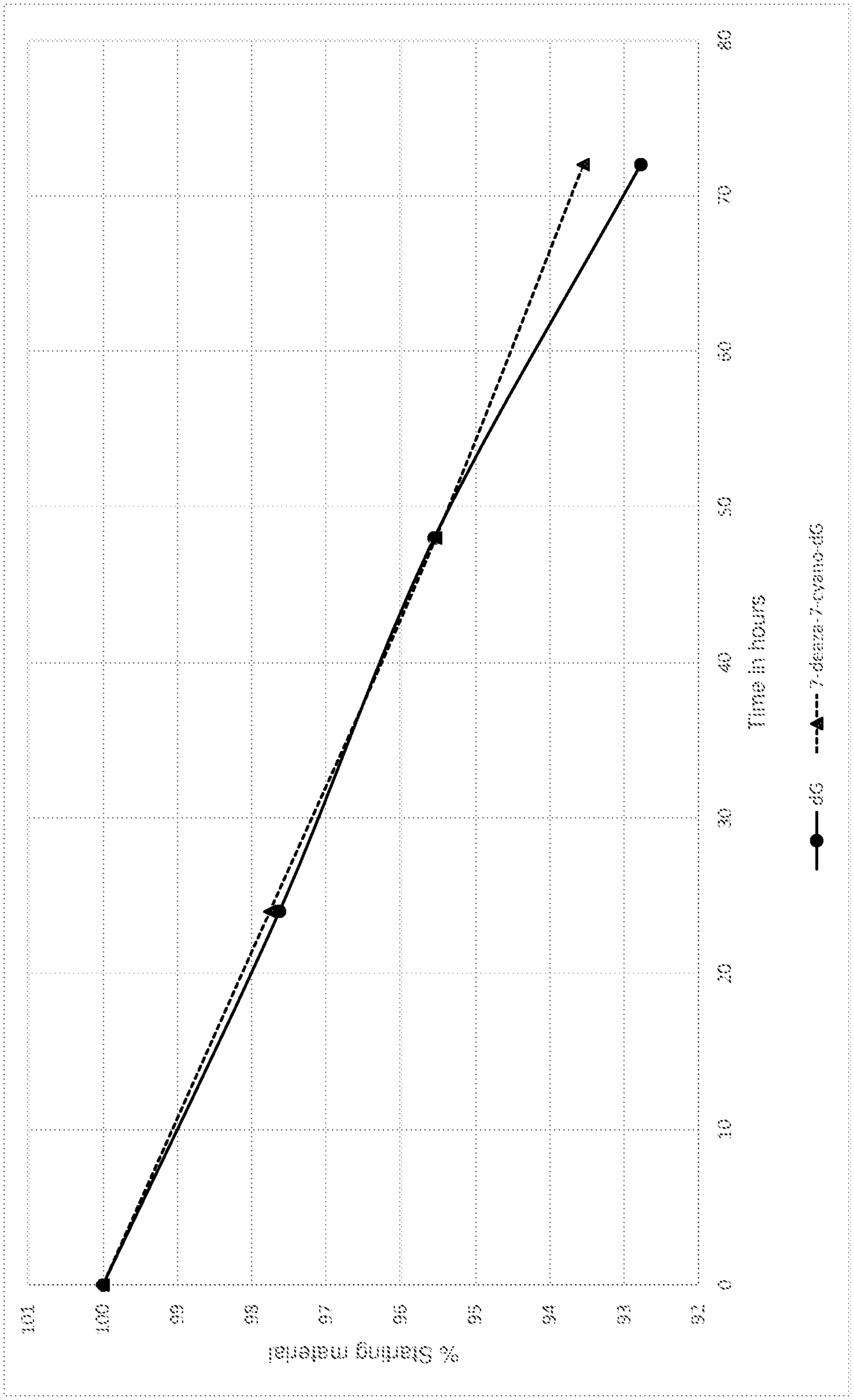

FIG. 9: Graph showing the stability of dG and 7-Deaza-7-Cyano-dG in NDS.

Figure 10:
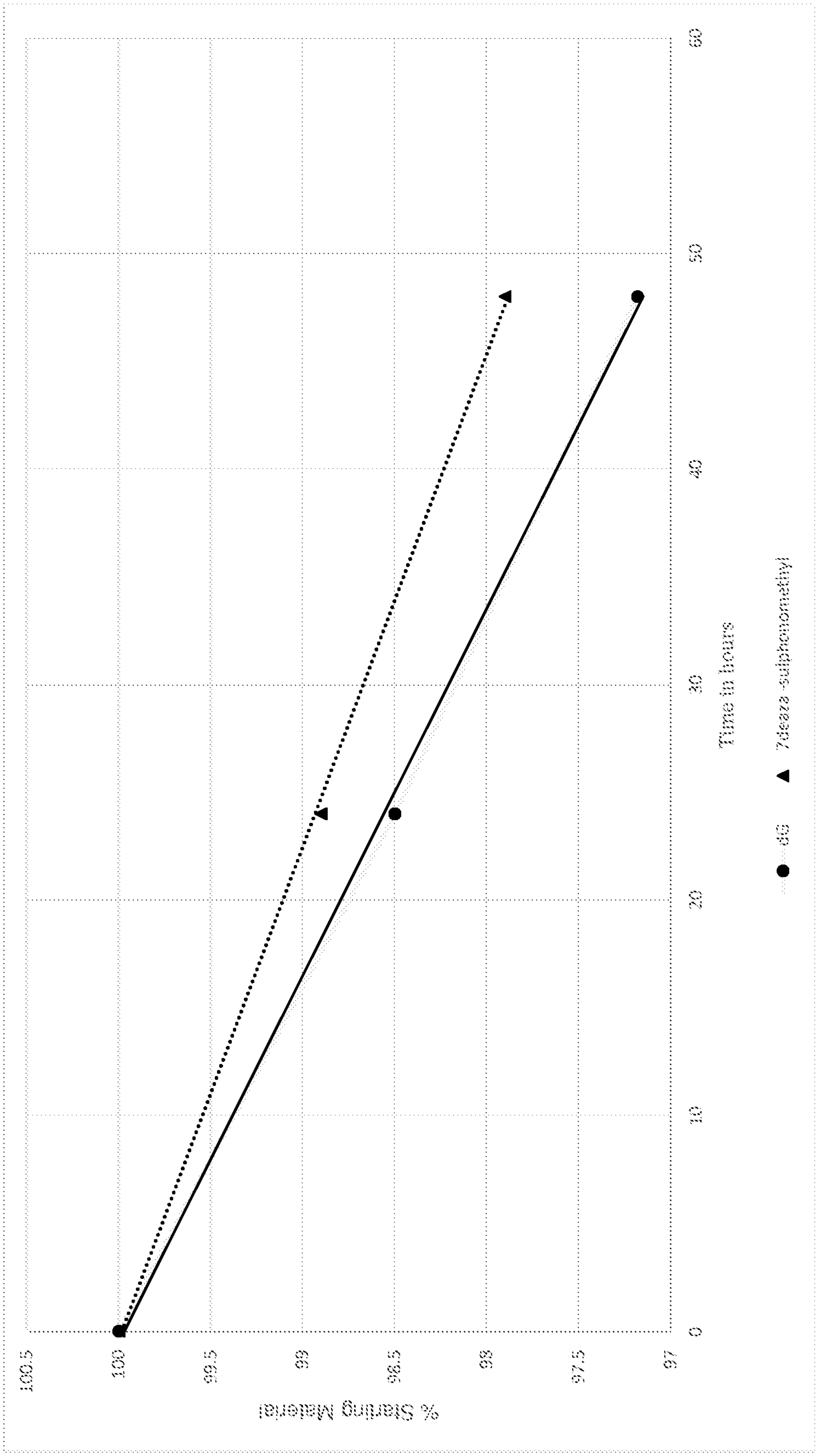

FIG. 10: Graph showing the stability of dG and 7-Deaza-7-$MeSO_2$-dG in NDS.

Figure 11:
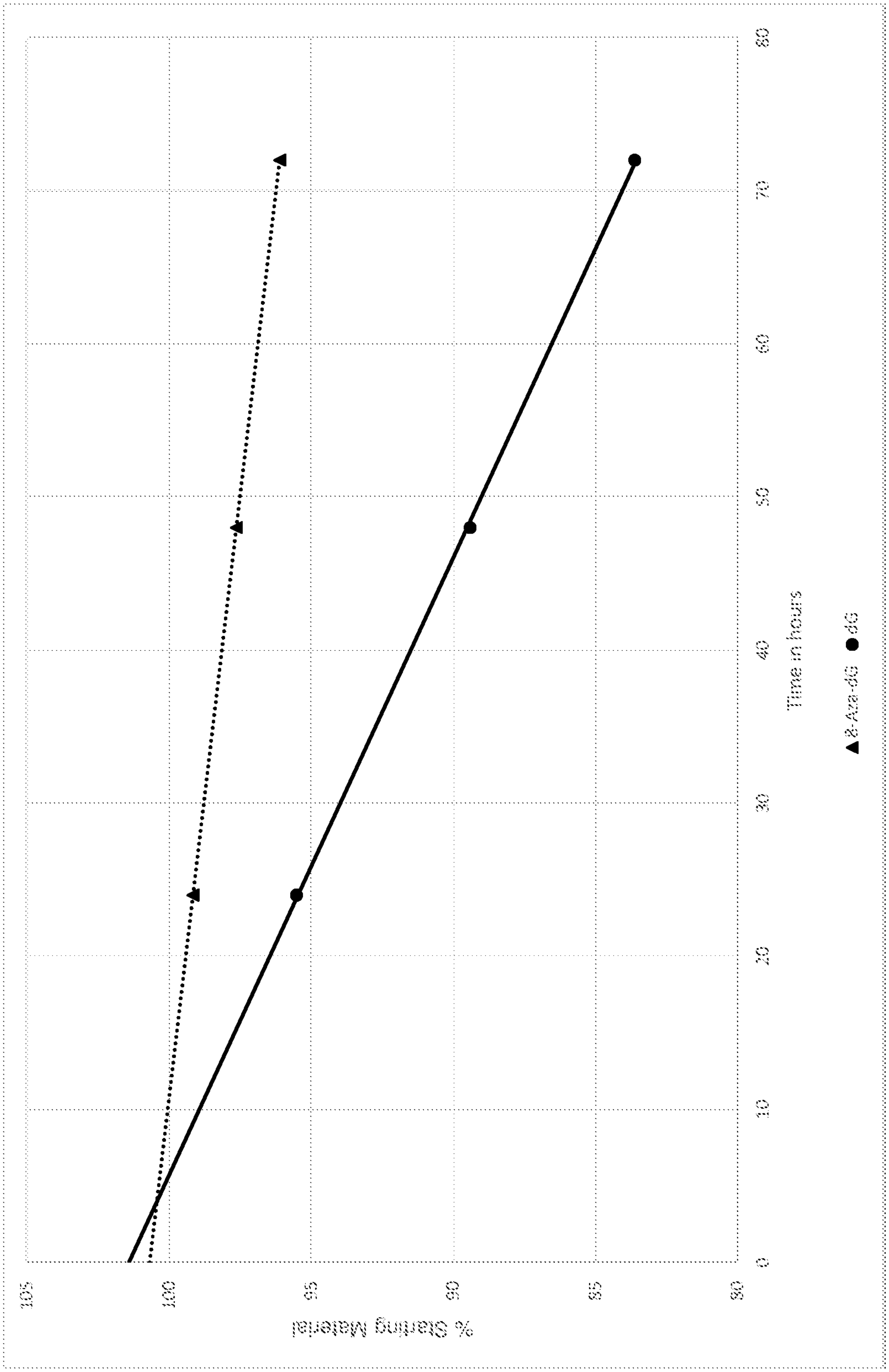

FIG. 11: Graph showing the stability of dG and 8-Aza-dG in NDS at rt.

Figure 12:
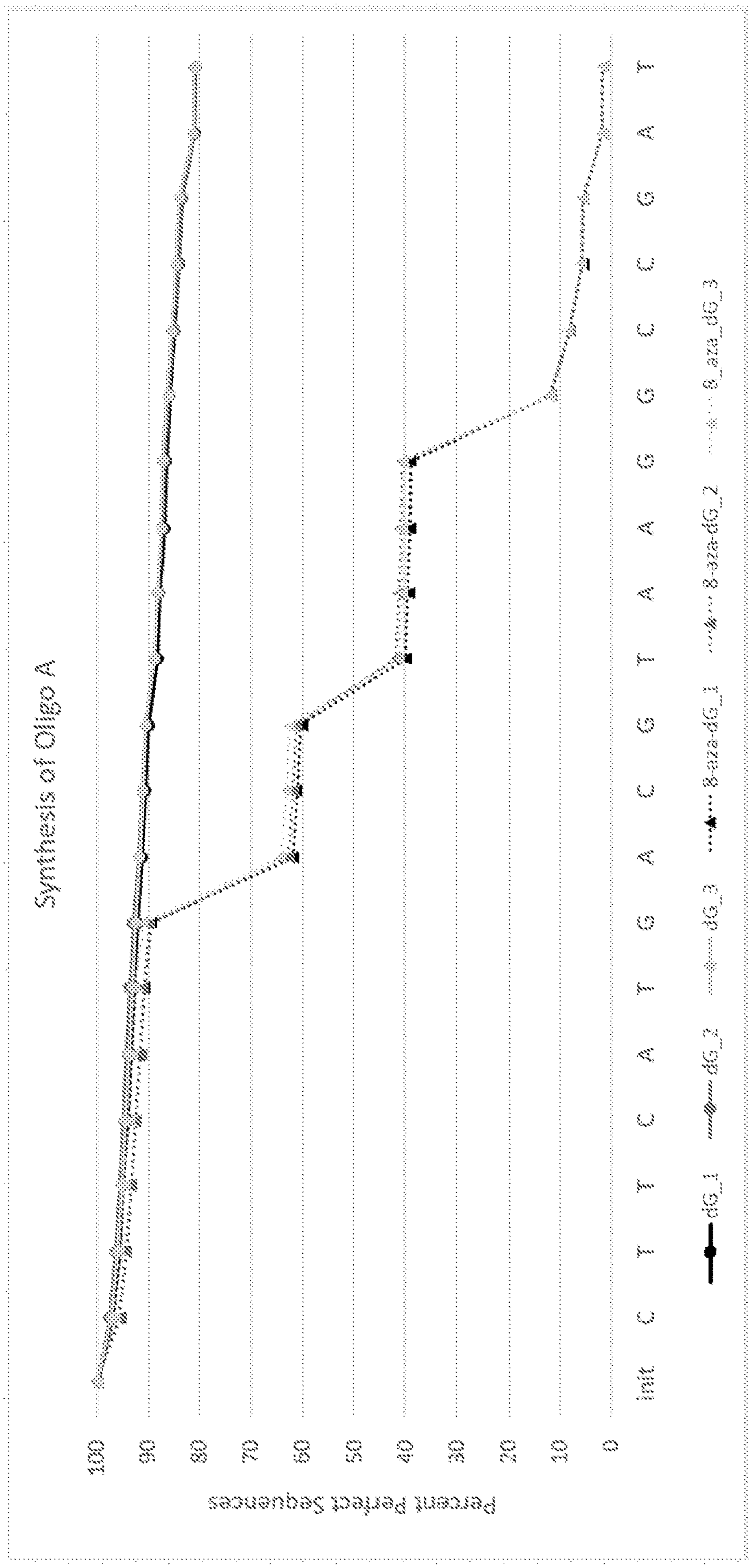

FIG. 12: Graph showing the synthesis of Oligo A.

Figure 13:
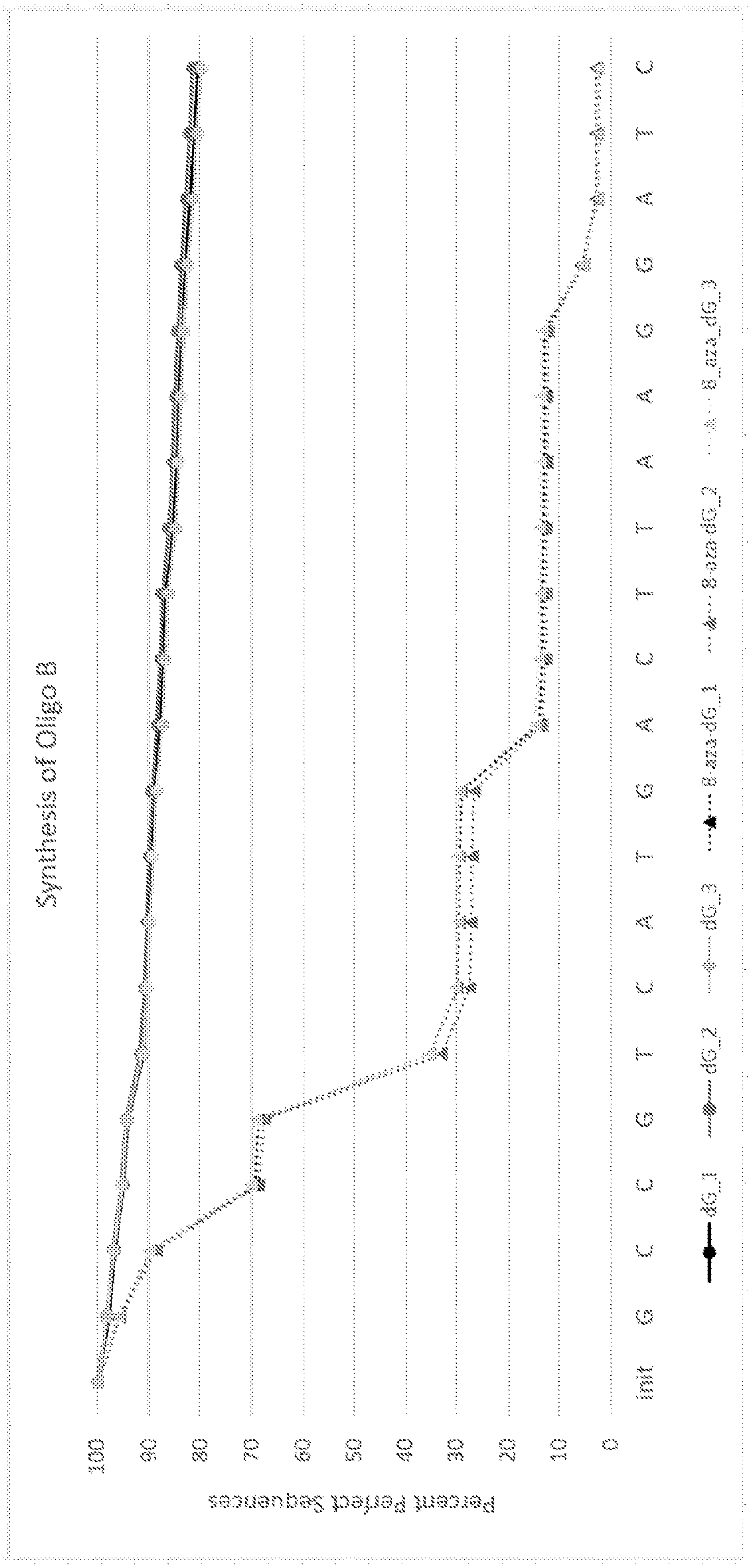

FIG. 13: Graph showing the synthesis of Oligo B.

EXAMPLES

3',5'-Di-(O)-p-Toluoyl-2(N)-Dibenzoyl-4(O)-Methyl-7-Deaza-2'-Deoxyguanosine

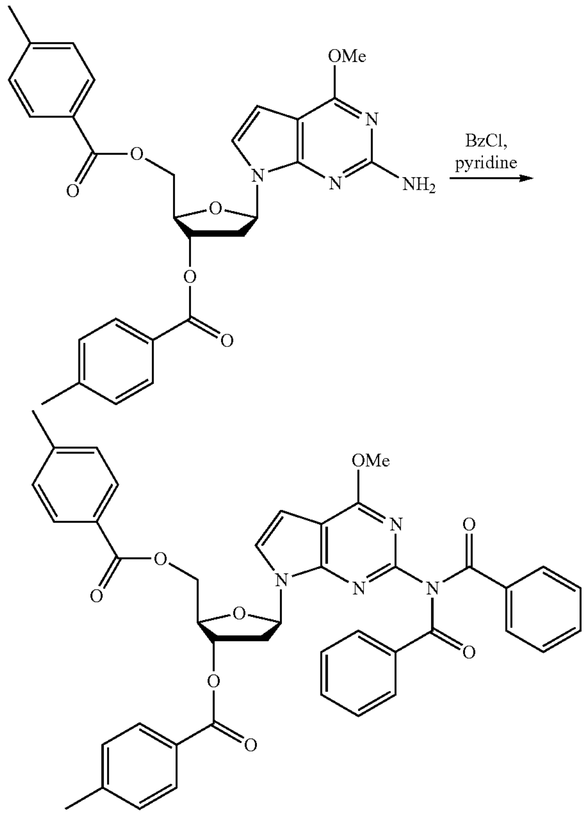

3',5'-Di-(O)-p-toluoyl-4(O)-methyl-7-deaza-2'-deoxyguanosine (for preparation see Seela et al, *J. Chem. Soc., Perkin Trans. I*, (1988), 697-702) (6.0 g, 11.6 mmol) was co-evaporated with dry pyridine (5 ml) twice and resuspended in the same. The reaction was cooled in ice bath for approx. 20 min and benzoyl chloride (4.0 mL 23 mmol) was added dropwise. After the addition was finished the reaction was stirred in ice bath for 30 min and then at room temperature until the reaction was over. Saturated sodium bicarbonate was added and the product was extracted into DCM. The organic layers were pooled, dried, evaporated and the residue was chromatographed to give the pure product.

m/z ($ES^+$) 725 ([M+H], 100%).

$^1$H NMR (400 MHz, $CDCl_3$) δ(ppm) 7.97 (2H, d, J=8.2 Hz), 7.89 (2H, d J=8.3 Hz), 7.84 (4H, dd, J=8.2, 1.1 Hz), 7.44 (2H, tt, J=7.4, 1.2 Hz), 7.32 (4H, t, J=7.7 Hz), 7.28 (2H, d, J=8.1 Hz), 7.22 (2H, d, J=8.0 Hz), 7.14 (1H, d, J=3.7 Hz), 6.47 (1H, dd, J=8.4, 5.8 Hz), 6.43 (1H, d, J=3.7 Hz), 5.61 (1H, dt, J=6.2, 2.1 Hz), 4.63 (2H, m), 4.52 (1H, td, J=4.2, 2.4 Hz), 3.76 (3H, s), 2.57 (1H, ddd, J=14.6, 8.3, 6.3 Hz), 2.44 (1H, m), 2.43 (3H, s) and 2.41 (3H, s).

3',5'-Di-(O)-p-Toluoyl-2(N)-Dibenzoyl-4(O)-Methyl-7-Deaza-7-Iodo-2'-Deoxyguanosine

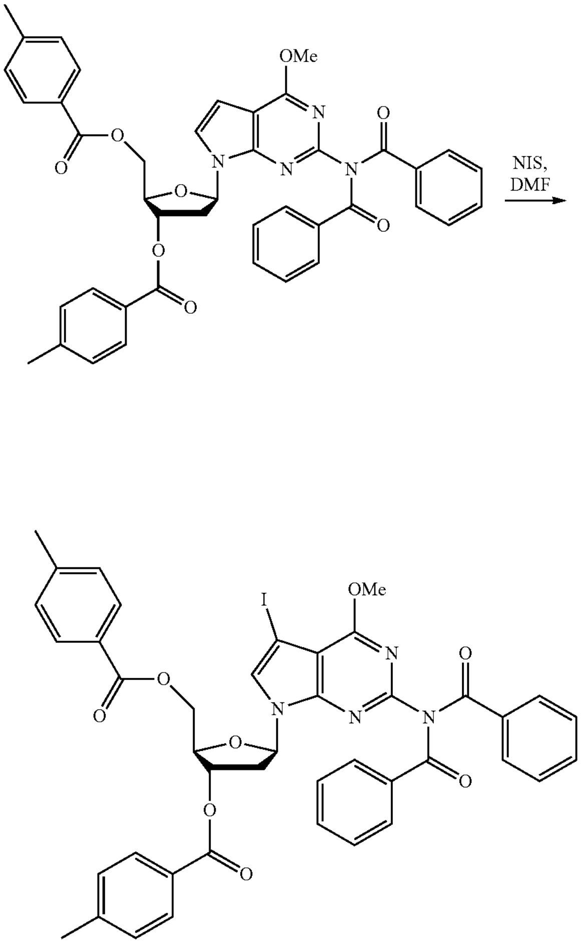

To a solution of 3',5'-di-(O)-p-toluoyl-2(N)-dibenzoyl-4(O)-methyl-7-deaza-2'-deoxyguanosine (1.57 g, 2.60 mmol) in anhydrous DMF (5.0 mL) was added N-iodosuccinimide (0.6 g, 2.16 mmol) and the mixture was stirred for 12 h at room temperature. The resulting red solution was concentrated to give a residual red oil that was partitioned between diethyl ether (20 mL) and saturated aqueous sodium bicarbonate solution (20 mL). The layers were separated and the aqueous layer was extracted with diethyl ether (2×25 mL). The combined organic layers were washed with water (4×50 mL), saturated brine (50 mL), dried ($MgSO_4$) and concentrated to give a brown solid. This material was purified under normal phase conditions (silica column, gradient of ethyl acetate in hexane) and repurified with hexane-methyl tert-butyl ether to give pure product.

m/z ($ES^+$) 851 ([M+H], 100%).

$^1$H NMR (400 MHz, $CDCl_3$ δ(ppm) 7.96 (2H, d, J=8.2 Hz), 7.90 (2H, d, J=8.2 Hz), 7.81 (4H, dd, J=8.4, 1.3 Hz), 7.45 (2H, tt, J=7.4, 1.2 Hz), 7.33 (4H, t, J=7.7 Hz), 7.28 (2H, d, J=8.0 Hz), 7.26 (2H, d, J=8.0 Hz), 7.24 (2H, d, J=8.0 Hz), 7.17 (1H, s), 6.41 (1H, dd, J=7.7, 6.3 Hz), 5.58 (1H, dt, J=5.3, 2.6 Hz), 4.65 (2H, m), 4.51 (1H, td, J=3.8, 2.4 Hz), 3.77 (3H, s), 2.43 (3H, s), 2.42 (3H, s) and 2.40 (2H, m).

7-Deaza-7-Trifluoromethyl-2'-Deoxyguanosine

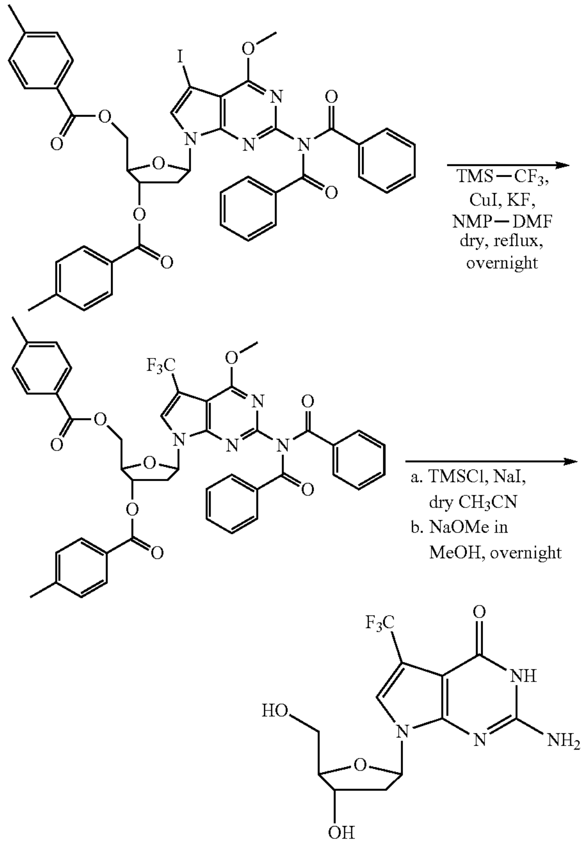

The trifluoromethylation reaction was carried out according to the procedure described in Hulpia et al, *Eur. J. Med. Chem* 188 (2020), 112018. Thus, $TMSCF_3$ (0.19 mL, 1.3 mmol, 3.0 eq.) was added dropwise over the course of 1 h to a suspension of CuI (0.521 g, 1.30 mmol, 1.0 eq.) and KF (0.076 g, 1.3 mmol, 3.0 eq.) in a mixture of dry degassed DMF/NMP 1:1 (3 mL); when all solids had dissolved, iodo nucleoside (0.31 g, 0.43 mmol, 1.0 eq.) in dry degassed DMF/NMP 1:1 (3 mL) was added, and the mixture was heated to reflux. After 3 h, LC/MS analysis showed full conversion of the starting material, and the reaction was cooled to room temperature. The mixture was diluted with EtOAc (15 mL) and $H_2O$ (5 mL) and the solids were filtered off over Celite®. The filter cake was washed extensively with additional EtOAc (3×25 mL), and the combined filtrates were transferred to a separation funnel. Additional water (40 mL) was added, the phases separated, and the organic phase washed twice more with water (25 mL). The organic layer was dried over $Na_2SO_4$ and concentrated in vacuo.

The material so obtained was taken forward to the next step of ester and amide deprotection.

Done in two steps—In the first step the crude trifluoromethylated nucleoside was dissolved in dry MeOH and then 5.4 M NaOMe was added to it and left to stir overnight. TLC indicated that the starting material had all disappeared. Glacial acetic acid was then added, and the solvents were evaporated. The residue was again evaporated with toluene to remove acetic acid.

This residue was then co evaporated with 5 mL of dry acetonitrile thrice and then dissolved in the same. NaI was added and then TMSCl was added drop wise and left to stir. Aliquots were checked after 1, 2 and 3 h and the reaction was found to be complete in 3 h. The reaction was quenched with TEAB buffer and the solvents were evaporated. The crude was purified on a preparative C-18 column HPLC (RP C18 30×250 100PC) using 10% aq. TEAB buffer and $CH_3CN$ to obtain the product as a white fluffy powder in 20% overall yield after 3 steps $^1$H NMR (400 MHz, $D_2O$): δ7.38 (q, J=1.6 Hz, 1H), 6.31 (dd, J=7.7, 6.2 Hz, 1H), 4.49 (dt, J=6.3, 3.3 Hz, 1H), 4.00 (dt, J=4.8, 3.6 Hz, 1H), 3.75-3.60 (m, 2H), 3.05 (q, J=7.3 Hz, 4H), 2.57 (ddd, J=14.0, 7.8, 6.3 Hz, 1H), 2.35 (ddd, J=14.1, 6.3, 3.4 Hz, 1H). 19F NMR (376 MHz, $D_2O$): δ−57.41.

7-Deaza-7-Cyano-2'-Deoxyguanosine

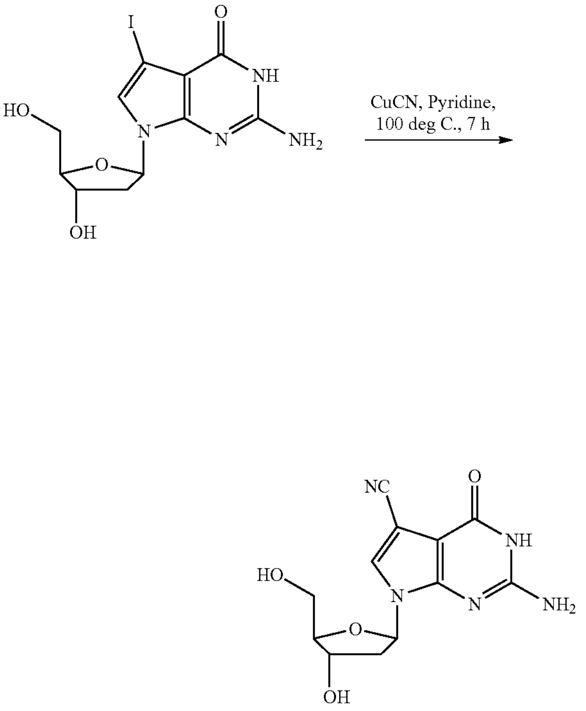

7-Deaza-7-cyano dG was prepared as reported in Ramzaeva, N. et al. "Facile Synthesis of 2'-Deoxynucleoside Analogs of preQ." *Synthesis*, (1998): 1327-1330. 2-Amino-5-cyano-7-(2-deoxy-α-D-erythro-pentofuranosyl)-3,7-dihydro-4H-pyrrolo[2,3-d]pyrimidin-4-one: A suspension of 7-iodo-7-deaza-dG (360 mg, 0.9 mmol) and CuCN (500 mg, 5.6 mmol) in pyridine (4 mL) was heated at 100° C. for 7 h. The mixture was cooled, diluted with $CH_2Cl_2$/MeOH (8:2), filtered and evaporated. The yellow residue was then dissolved in water and purified on Äkta with C-18 column using 0.1% AcOH-water and ACN as mobile phase. Yield-4.0%

$^1$H NMR (400 MHz, DMSO-d6): δ11.00 (s, 1H), 7.83 (s, 1H), 6.61 (s, 2H), 6.20 (dd, J=7.9, 5.9 Hz, 1H), 5.21 (s, 1H), 4.92 (s, 1H), 4.23 (s, 1H), 3.72 (td, J=4.5, 2.4 Hz, 1H), 3.44 (dq, J=11.8, 6.0 Hz, 2H), 2.26 (ddd, J=13.3, 8.0, 5.7 Hz, 1H), 2.09 (ddd, J=13.1, 5.9, 2.9 Hz, 1H).

3',5'-Di-(O)-(tert-Butyldimethylsilyl)-7-Deaza-7-Iodo-2'-Deoxyguanosine

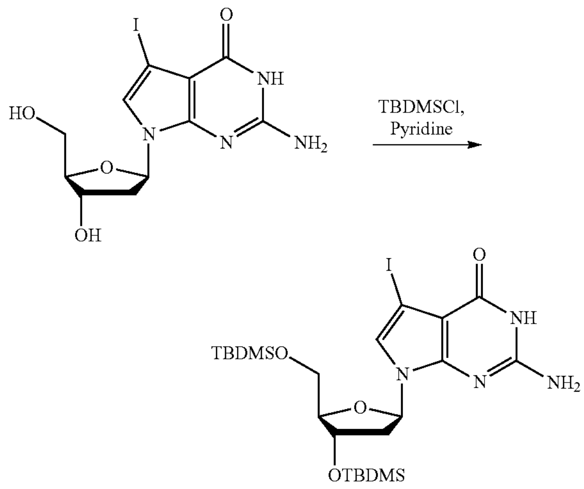

7-Deaza-7-iodo-2'-deoxyguanosine (329 mg, 0.84 mmol) and imidazole (0.40 g, 5.87 mmol) were placed in a reaction flask, which was purged with nitrogen, then anhydrous pyridine (2.5 mL) was added. The solution was cooled in an ice-water bath, then tert-butyldimethylchlorosilane (506 mg, 3.36 mmol) was added in a single portion. The solution was stirred in an ice-water bath for 10 minutes, allowed to warm to room temperature and stirred for 3 h. Methanol (0.24 mL) was added over 2 minutes, then the solution was stirred at room temperature for 30 minutes. Toluene (10 mL) and water (10 mL) were added. The layers were separated and the aqueous phase was extracted with toluene (2×5 mL). The combined organic phases were dried ($MgSO_4$) and filtered. The solvent was evaporated, toluene (10 mL) was added, then the solvent was evaporated again. This was repeated to give 3',5'-di-(O)-(tert-butyldimethylsilyl)-7-deaza-7-iodo-2'-deoxyguanosine as a white, extremely viscous, glassy oil (574 mg, 110%).

m/z ($ES^+$) 621 ([M+H], 100%). m/z ($ES^-$) 619 ([M−H], 100%).

$^1H$ NMR ($CD_3CN$, 400 MHz) δ(ppm) 8.85 (1H, br s), 7.00 (1H, s), 6.29 (1H, dd, J=7.8, 6.1 Hz), 5.25 (2H, br s), 4.50 (1H, dt, J=5.6, 2.9 Hz), 3.84 (m), 3.716 (1H, d, J=3.8 Hz), 3.714 (1H, d, J=4.1 Hz), 2.36 (1H, ddd, J=13.3, 7.7, 5.6 Hz), 2.19 (1H, ddd, J=13.3, 6.1, 3.2 Hz), 0.92 (9H, s), 0.91 (9H, s), 0.11 (9H, s) and 0.10 (9H, s).

3',5'(O)-Di-(tert-Butyldimethylsilyl)-7-(Methanesulfonyl)-7-Deaza-2'-Deoxyguanosine

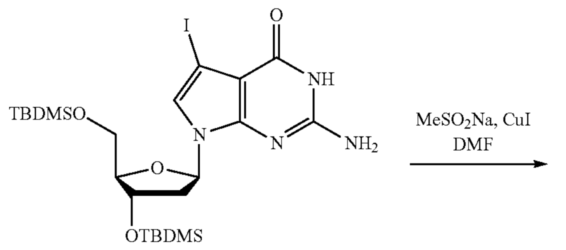

-continued

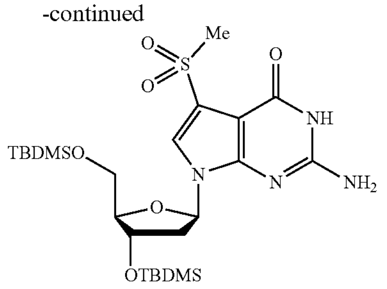

3',5'-Di-(O)-(tert-butyldimethylsilyl)-7-deaza-7-iodo-2'-deoxyguanosine (291 mg, 0.47 mmol), methanesulfinic acid sodium salt (191 mg, 1.88 mmol) and copper(I) iodide (134 mg, 0.70 mmol) were placed in a reaction flask, which was purged with nitrogen, then anhydrous DMF (1.5 mL) was added. The suspension was heated in a metal heating block heated at 100° C. for 4.5 h. Toluene (10 mL) and water (10 mL) were added. The layers were separated, and the aqueous layer was extracted with toluene (2×10 mL). The combined organic layers were dried ($MgSO_4$) and filtered. The solvent was evaporated, and the residue was combined with a previous sample made using the same procedure, starting with 3',5'-di-(O)-(tert-butyldimethylsilyl)-7-deaza-7-iodo-2'-deoxyguanosine (40 mg, 0.064 mmol), methanesulfinic acid sodium salt (26 mg, 0.26 mmol), copper(I) iodide (18 mg, 0.10 mmol) and anhydrous DMF (0.2 mL) and purified using flash chromatography on a 24 g silica cartridge, eluting with a dichloromethane to dichloromethane-methanol (95:5) gradient to give 3',5'-di-(O)-(tert-butyldimethylsilyl)-7-(methanesulfonyl)-7-deaza-2'-deoxyguanosine as pale yellow, extremely viscous, glassy oil (91 mg, 30%).

m/z ($ES^+$) 573 ([M+H], 100%). m/z ($ES^-$) 571 ([M−H], 100%).

$^1H$ NMR (400 MHz, $CD_3CN$) δ(ppm) 9.18 (1H, br s), 7.46 (1H, s), 6.32 (1H, dd, J=8.1, 5.9 Hz), 5.44 (2H, br s), 4.51 (1H, td, J=5.4, 2.7 Hz), 3.90 (1H, m), 3.75 (2H, d, J=3.9 Hz), 3.28 (3H, s), 2.52 (1H, ddd, J=13.4, 8.0, 5.5 Hz), 2.24 (1H, ddd, J=13.2, 5.9, 2.8 Hz), 0.92 (9H, s), 0.90 (9H, s), 0.11 (6H, s), 0.091 (3H, s) and 0.087 (3H, s).

7-(Methanesulfonyl)-7-Deaza-2'-Deoxyguanosine

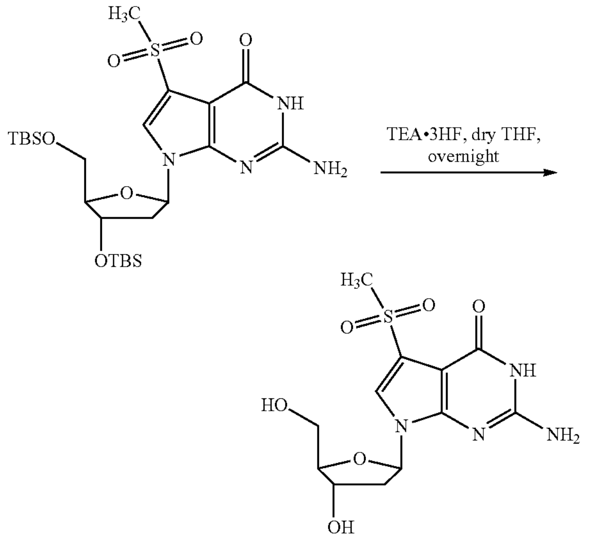

Silyl protected nucleoside (0.080 g, 0.14 mmol) was taken in a 50 ml RB and dissolved in 1.0 mL dry THF. TEA·3HF 0.1 ml, 3 eq.) was added dropwise and reaction was left to stir overnight. After completion, the reaction was worked up with addition of 5.0 mL of ethoxytrimethylsilane to quench excess reagent and precipitate the product. A sticky precipitate was obtained. The precipitate was then dissolved in water and purified on C-18-RP prep column (RP C18 30×250 mm, 100PC) using 0.1% acetic acid in water and ACN as the mobile phase yielding approx. 10 mg of white fluffy product after lyophilization.

$^1$H NMR (400 MHz, DMSO-d6): δ11.00 (s, 1H), 7.83 (s, 1H), 6.61 (s, 2H), 6.20 (dd, J=7.9, 5.9 Hz, 1H), 5.21 (s, 1H), 4.92 (s, 1H), 4.23 (s, 1H), 3.72 (td, J=4.5, 2.4 Hz, 1H), 3.44 (dq, J=11.8, 6.0 Hz, 2H), 2.26 (ddd, J=13.3, 8.0, 5.7 Hz, 1H), 2.09 (ddd, J=13.1, 5.9, 2.9 Hz, 1H).

Stability Tests of Modified 2'-Deoxyguanosines in NDS Buffer vs. 2'-Deoxyguanosine

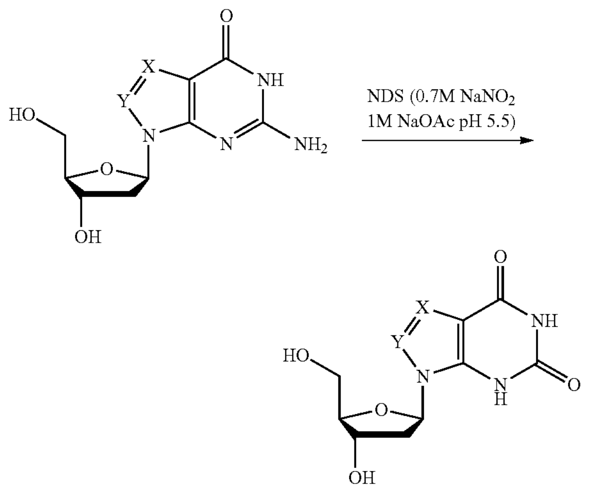

Nitrite deprotection solution (NDS) was prepared from sodium nitrite (380 mg, 5.5 mmol) and 1M pH 5.5 sodium acetate (7.868 mL) and adjusted to pH 5.5 with 10M sodium hydroxide. Samples of nucleoside (~0.5 mg) were dissolved in 1 mL aliquots of this buffer. The samples were analysed by HPLC or LC/MS using Method 1 or Method 2 immediately after making up the samples and at intervals over 4 days while stored at room temperature alongside reference samples of 2'-deoxyguanosine. 2'-Deoxyguanosine gave an approximately 8:1 mixture of 2'-deoxyxanthosine and Peak (3) with the same mass as 2'-deoxyxanthosine. 7-Deaza-2'-deoxyguanosine gave 7-deaza-2'-deoxyxanthosine as one component of a complex mixture of products. Other nucleosides gave products with masses corresponding to the products of substitution of $NH_2$ with OH (increase of 1 Da) assigned to the 2'-deoxyxanthosine analogues. Data for 7-deaza-2'-deoxyguanosine (X═CH, Y═CH), 7-deaza-7-trifluoromethyl-2'-deoxyguanosine (X═$CCF_3$, Y═CH), 7-deaza-7-cyano-2'-deoxyguanosine, 7-deaza-7-methanesulfonyl-2'-deoxyguanosine (X═$CSO_2Me$, Y═CH) and 8-aza-2'-deoxyguanosine (X═N, Y═N) for experiments run in parallel with 2'-deoxyguanosine (X═CH, Y═N) are shown in the plots below. 7-Deaza-2'-deoxyguanosine is much less stable in NDS than 2'-deoxyguanosine, while 7-deaza-7-trifluoromethyl-2'-deoxyguanosine, 7-deaza-7-cyano-2'-deoxyguanosine and 7-deaza-7-methanesulfonyl-2'-deoxyguanosine are slightly more stable than 2'-deoxyguanosine. 8-Aza-2'-deoxyguanosine is more stable in NDS than 2'-deoxyguanosine by a factor of 4.2.

Method (1) for HPLC and LC/MS Analysis

| | |
|---|---|
| Column: | Ascentis Express C18 15 × 4.6 mm, 5 μm |
| Column temperature | 30° C. |
| Flow rate | 1 mL/min |
| Injection volume | 5 μL |
| UV detection | 254 nm |
| 20 mM $NH_4OAc$ pH 4.5 | A |
| Acetonitrile | B |
| **Time (min)** | **% B** |
| 0 | 1 |
| 1 | 1 |
| 10 | 50 |
| 12 | 50 |
| 13 | 1 |
| 15 | 1 |

Retention Times Using Method (1) (min)

| | |
|---|---|
| 2'-Deoxyguanosine (X = N, Y = CH) | 4.06 |
| 2'-Deoxyxanthosine (X = N, Y = CH) | 4.25 |
| Peak (3) from reaction of 2'-deoxyguanosine | 4.72 |
| 8-Aza-2'-deoxyxanthosine (X = N, Y = CN) | 4.62 |
| 8-Aza-2'-deoxyguanosine (X = N, Y = CN) | 5.10 |
| 7-Deaza-2'-deoxyguanosine (X = CH, Y = CH) | 5.20 |
| 7-Deaza-2'-deoxyxanthosine (X = CH, Y = CH) | 5.61 |
| 7-Deaza-7-trifluoromethyl-2'-deoxyguanosine (X = $CCF_3$, Y = CH) | 6.72 |
| 7-Deaza-7-trifluoromethyl-2'-deoxyxanthosine (X = $CCF_3$, Y = CH) | 7.17 |

Mass Spectra Recorded for Compounds Above

2'-Deoxyguanosine m/z ($ES^+$) 268 ([M+H], 94%), 535 ([2M+H], 100); m/z ($ES^-$) 266 ([M−H], 60%) and 533 ([2M−H], 100).

2'-Deoxyxanthosine m/z ($ES^+$) 269 ([M+H], 34%), 535 ([2M+H], 44), 537 ([2M+H], 100) and 559 ([2M+Na], 20); m/z ($ES^-$) 267 ([M−H], 29%) and 535 ([2M−H], 100).

Peak (3) from 2'-deoxyguanosine m/z ($ES^+$) 269 ([M+H], 100%); m/z ($ES^-$) 267 ([M−H], 100%).

8-Aza-2'-deoxyxanthosine m/z ($ES^-$) 268 ([M−H], 54%) and 537 ([2M−H], 100).

8-Aza-2'-deoxyguanosine m/z ($ES^-$) 267 ([M−H], 56%) and 535 ([2M−H], 100).

7-Deaza-2'-deoxyguanosine m/z ($ES^+$) 267 ([M+H], 100% and 555 ([2M+Na], 10); m/z ($ES^-$) 265 ([M−H], 36%) and 531 ([2M−H], 100).

7-Deaza-2'-deoxyxanthosine m/z ($ES^+$) 268 ([M+H], 100%); m/z ($ES^-$) 267 ([M−H], 100%).

7-Deaza-7-trifluoromethyl-2'-deoxyguanosine m/z ($ES^+$) 335 ([M+H], 100%) and 691 ([2M+Na], 36%).

7-Deaza-7-trifluoromethyl-2'-deoxyguanosine m/z ($ES^+$) 336 ([M+H], 100%) and 693 ([2M+Na], 15%).

Method (2) for HPLC and LC/MS Analysis

| | |
|---|---|
| Column: | Ascentis Express C18 15 × 4.6 mm, 5 μm |
| Column temperature | 30° C. |
| Flow rate | 1 mL/min |
| Injection volume | 5 μL |
| UV detection | 254 nm |
| 20 mM $NH_4OAc$ pH 4.5 | A |
| Acetonitrile | B |

| Time (min) | % B |
|---|---|
| 0 | 1 |
| 4 | 1 |
| 18 | 8 |
| 20 | 30 |
| 21 | 1 |
| 22 | 1 |

Retention Times Using Method (2) (min)

| | |
|---|---|
| 7-Deaza-7-methanesulfonyl-2'-deoxyguanosine (X = $CSO_2Me$, Y = CH) | 12.91 |
| 7-Deaza-7-methanesulfonyl-2'-deoxyxanthosine (X = $CSO_2Me$, Y = CH) | 13.74 |
| 7-Deaza-7-cyano-2'-deoxyguanosine (X = CCN, Y = CH) | 15.03 |
| 7-Deaza-7-cyano-2'-deoxyxanthosine (X = CCN, Y = CH) | 16.22 |

Mass Spectra Recorded for Compounds Above

7-Deaza-7-methanesulfonyl-2'-deoxyguanosine m/z ($ES^+$) 345 ([M+H], 75%), 367 ([M+H], 20%), 689 ([2M+H], 64) and 711 ([2M+Na], 100); m/z ($ES^-$) 343 ([M−H], 75%) and 687 ([2M−H], 100).

7-Deaza-7-methanesulfonyl-2'-deoxyxanthosine m/z ($ES^+$) 346 ([M+H], 100%) and 368 [(2+Na], 53); m/z ($ES^-$) 344 ([M−H], 100).

7-Deaza-7-cyano-2'-deoxyguanosine m/z ($ES^+$) 292 ([M+H], 83%), 583 ([2M+H], 100) and 605 ([2M+Na], 53).

7-Deaza-7-cyano-2'-deoxyxanthosine m/z ($ES^+$) 310 ([M+$NH_4$-], 100%; 607 [(2M+Na], 54) m/z ($ES^-$) 292 ([M−H], 100) and 583 ([2M−H], 62).

Synthesis of N2-((Dimethylamino)methylene)-8-Aza-2'-Deoxyguanosine

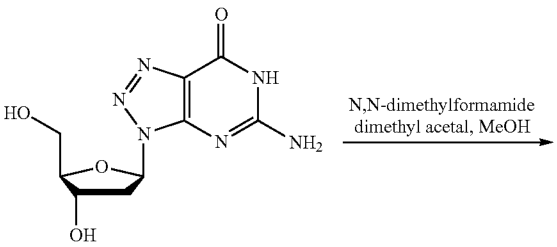

-continued

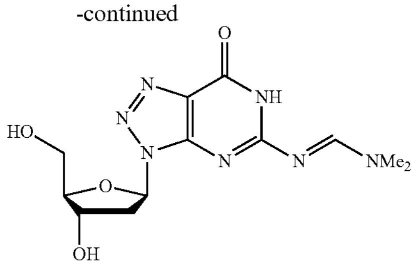

Commercial 8-aza-2'-deoxyguanosine (2 g, 7.5 mmol) was azeotropically dried with anhydrous MeOH (1×20 mL) and suspended in anhydrous MeOH (30 mL). The resultant suspension was vigorously stirred and N,N-dimethylformamide dimethyl acetal (2.22 g, 18.6 mmol, 2.48 mL) was added in one portion. The reaction was allowed to stir at room temperature. After 2 h the reaction was diluted with methyl-tert-butyl ether (20 mL) and the precipitate was collected, washed with methyl-tert-butyl ether (2×5 mL) and dried under high vacuum. The product was obtained as a pale yellow solid (2.3 g, 96%).

$^1H$ NMR (DMSO-d6, 400 MHz) δ8.70 (s, 1H, CH of imine), 6.45 (dd, 1H, H-1'), 5.78 (br s, 1H, 5'-OH), 5.40 (br s, 1H, 3'-OH), 4.81-4.77 (m, 1H, H3'), 4.50-4.47 (m, 1H, H4'), 3.89-3.75 (m, 1H, H5'), 3.6-3.48 (m, 1H, H5") 3.24, 3.03 (2×s, 6H, 2×—$CH_3$), 2.90-2.89 (m, 1H, H2'), 2.39-2.33 (m, 1H, H2").

Synthesis of N2-((Dimethylamino)methylene)-3',5'-O-(4-Nitrobenzoate) 8-Aza-2'-Deoxyguanosine

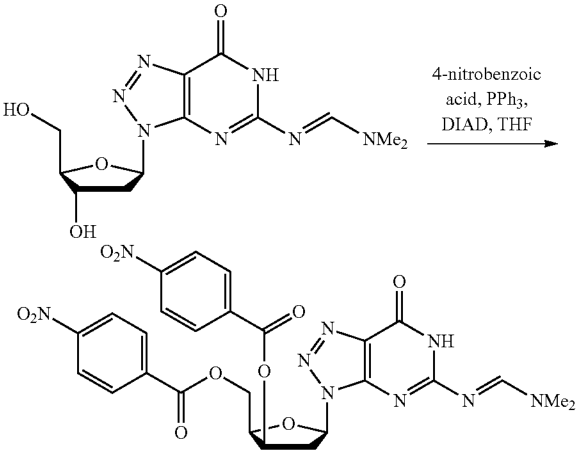

N2-((Dimethylamino)methylene)-8-aza-2'-deoxyguanosine (2.2 g, 0.0068 mol), 4-nitrobenzoic acid (3.41 g, 0.0204 mol), triphenylphosphine (5.71 g, 0.0218 mol) was placed into round bottom flask and anhydrous THF (40 mL) was added. To a stirred suspension diisopropyl azodicarboxylate (DIAD) (4.29 mL, 4.40 g, 0.0218 mol) was added drop by drop over 3 min, maintaining the temperature at 10° C. and the resultant mixture was allowed to stir at room temperature. After 18 h a clear solution was quenched by addition of water (10 mL) followed by evaporation of solvents using a rotary evaporator. The gummy residue was treated with 50 mL of isopropanol and vigorously stirred for 1 h when yellowish precipitate formed. The solid was filtered off and washed with iPrOH (2×10 mL). The product was obtained as a pale yellow solid (3.8 g, 90%).

$^1$H NMR (DMSO-d6, 400 MHz) δ8.59 (s, 1H, CH of imine), 7.52-8.4 (m, 8H of 4-$NO_2$-Bz group), 6.52-6.57 (m, 1H, H-1'), 5.84-5.79 (m, 1H, H3'), 4.80-4.73 (m, 1H, H4'), 4.65-4.55 (m, 1H, H5', H5"), 3.05, 3.14 (2×s, 6H, 2×—$CH_3$).

Synthesis of N2-((Dimethylamino)methylene)-xylo-8-Aza-2'-Deoxyguanosine

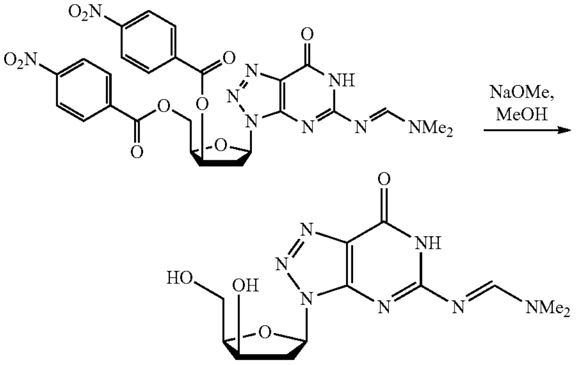

N2-((dimethylamino)methylene)-3',5'-di-(4-nitrobenzoate)-xylo-8-aza-2'-deoxyguanosine (3.8 g, 6.1 mmol) was suspended in methanol (30 mL). Triethylamine (8.52 mL, 61.1 mmol) was added and the reaction was heated to reflux for 30 min when a clear yellow solution resulted. The solution was allowed to cool down to room temperature and MTBE was added (5 mL). The mixture was allowed to stir at room temperature for 2 h when white solid precipitate formed. The solid was collected by filtration, washed with methyl-tert-butyl ether (3×5 mL) and dried under vacuum. N2-((Dimethylamino)methylene)-xylo-8-aza-2'-deoxyguanosine was obtained as a white solid (1.4 g, 71%).

$^1$H NMR (DMSO-d6, 400 MHz) δ8.558 (s, 1H, CH of imine), 6.36-6.41 (m, 1H, H-1'), 5.53-5.6 (m, 1H, 5'-OH), 4.60-4.65 (brs, 1H, 3'-OH), 4.35-4.47 (m, 1H, H3'), 3.97-3.87 (m, 1H, H4'), 3.54-3.8 (m, 2H, H5', H5"), 3.11, 3.31 (2×s, 6H, 2×—$CH_3$), 2.75-2.90 (m, 1H, H2'), 2.5-2.68 (m, 1H, H2").

Synthesis of N2-((Dimethylamino)methylene)-5'-O-tert-Butyldimethylsilyl-xylo-8-Aza-2'-Deoxyguanosine

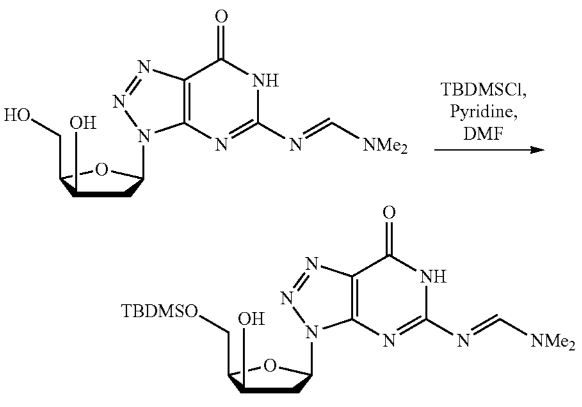

Substrate (1.4 g, 4.3 mmol) was dried under high vacuum for 2 h and then dissolved in anhydrous pyridine (8 mL) and DMF (2 mL). To a clear stirred solution mixture of TBDMSCl (0.78 g, 5.2 mmol) in DMF (2 mL) was added dropwise over 2 mins at room temperature. The resultant solution was allowed to stir at room temperature. After 30 minutes the reaction was quenched by addition of cold water (20 mL) when a white precipitate formed and the mixture was allowed to stir at rt for 1 h. Precipitate was collected by filtration and washed water (3×5 mL) and dried under high vacuum. The product was obtained as a white solid (1.8 g, 95%) in the mixture with 3',5'-O-TBDMS-((dimethylamino)methylene)-xylo-8-aza-2'-deoxyguanosine (6%) as a side product. This was not separated and the mixture was used in the next step.

$^1$H NMR (DMSO-d6, 400 MHz) δ8.85 (s, 1H, CH of imine), 8.40 (s, 1H, $H_8$), 6.25 (dd, 1H, H-1'), 5.63 (d, 1H, 3'-OH), 4.40-4.47 (m, 1H, H3'), 3.90-4.07 (m, 2H, H4', H5'), 3.75-3.84 (m, 1H, H5") 3.12, 3.20 (2×s, 6H, 2×—$CH_3$), 2.82-2.90 (m, 1H, H2'), 2.61-2.70 (m, 1H, H2"), 0.85 (s, 9H, Si—$C(CH_3)_3$), −0.02 (s, 6H, $Si(CH_3)_2$).

Synthesis of 3'-O-Phthalimido N2-((Dimethylamino)methylene)-5'-O-tert-Butyldimethylsilyl-xylo-8-aza-2'-Deoxyguanosine

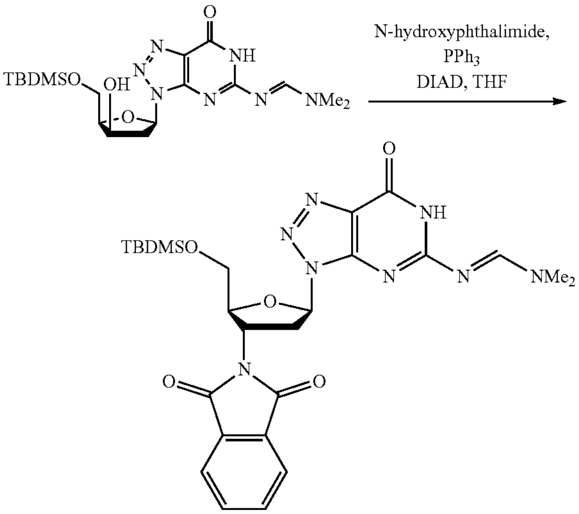

Substrate (1.72 g, 3.9 mmol) was dried under high vacuum for 3 hours and weighed into a flask with triphenylphosphine (1.65 g, 6.3 mmol) and N-hydroxyphthalimide (1.03 g, 6.3 mmol). Solids were dissolved in anhydrous THF (10 mL) to get a clear yellowish solution and the flask was immersed in a water-ice bath (~5° C.). To a resultant mixture DIAD (1.27 g, 6.3 mmol, 1.24 mL) was added dropwise over 5 min, maintaining temperature of the reaction at ~5° C. Upon completion of the addition the mixture turned yellow-orange and the flask was removed from the ice bath and the solution was allowed to stir at room temperature. After 40 min the reaction was quenched by addition of MeOH (5 mL) and concentrated using a rotary evaporator. The yellow liquor was diluted with ethyl acetate (20 mL) and washed with sodium bicarbonate solution (1×5 mL), water (2×5 mL), dried over $Na_2SO_4$, filtered and evaporated using a rotary evaporator. Product was isolated by flash column chromatography using gradient of AcOEt in hexane (0-50%). The product was obtained as a white solid (1.75 g) in the mixture with TPPO, alkene derivative and 3',5'-O-TBDMS-((dimethylamino)methylene)-xylo-8-aza-2'-deoxyguanosine. This was used in the next step without additional purification.

$^1$H NMR (DMSO-d6, 400 MHz) δ8.85 (s, 1H, CH of imine), 8.04-8.08 (m, 4H, phthalimide group), 6.75 (dd, 1H, H-1'), 5.32-5.36 (m, 1H, H3'), 4.58-4.50 (m, 1H, H4'), 3.80-3.73 (m, 2H, H5', H5"), 3.36, 3.23 (2×s, 6H, 2×—$CH_3$), 3.49-3.55 (m, 1H, H2'), 3.05-2.92 (m, 1H, H2"), 0.8 (s, 9H, Si—$C(CH_3)_3$), −0.05, −0.06 (2×s, 6H, $Si(CH_3)_2$).

Synthesis of 3'-(O)-Acetoxime-5'-O-tert-butyldimethylsilyl-8-Aza-2'-Deoxyguanosine

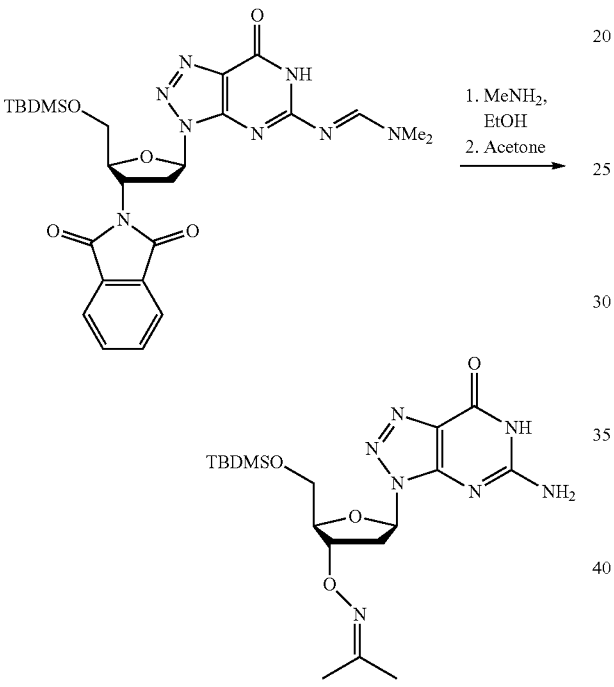

3'-(O)-Phthalimido-5'-O-TBDMS-N2-((dimethylamino)methylene)-8-aza-2'-deoxyguanosine (1.72 g, 3 mmol) was dissolved in MeOH (2 mL) and 33% ethanolic solution of methylamine was added (0.9 mL, 35 mmol). After 2 h, the reaction mixture was placed in a water bath and acetone (2.2 mL, 29.5 mmol) was slowly added. The reaction mixture was allowed to stir for the next 30 min. The reaction was diluted with ethyl acetate (10 mL) and extracted with a saturated solution of citric acid (2×1 mL) and water (1×1 mL). The organic phase was dried over $MgSO_4$, filtered and evaporated to dryness. The product was purified by flash column chromatography using gradient of MeOH in DCM (0-3%). 3'-(O)-Acetoxime-5'-O-tert-butyldimethylsilyl-8-aza-2'-deoxyguanosine was obtained as a white solid (0.8 g, 62%).

$^1$H NMR (DMSO-d6, 400 MHz) δ7.05 (br s, 2H, —$NH_2$), 6.38 (dd, 1H, H-1'), 4.98-4.92 (m, 1H, H3'), 4.28-4.20 (m, 1H, H4'), 3.85-3.65 (m, 2H, H5', H5"), 3.26-3.15 (m, 1H, H2'), 2.68-2.61 (m, 1H, H2"), 1.91 (s, 6H, 2×—$CH_3$ of oxime), 0.86 (s, 9H, Si—$C(CH_3)_3$), −0.09 (2×s, 6H, $Si(CH_3)_2$).

Synthesis of 3'-(O)-Acetoxime-8-Aza-2'-Deoxyguanosine

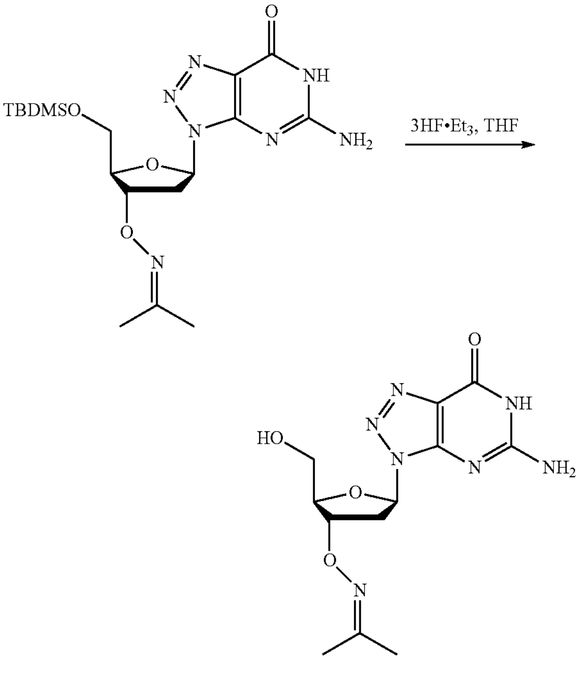

Substrate (0.6 g, 1.4 mmol) was dissolved in anhydrous THF (5 mL) and triethylamine trihydrofluoride (1.34 mL) was added. The resultant mixture was stirred overnight at room temperature. After 18 h ethoxytrimethylsilane (5 mL) was slowly added followed by addition of hexane (4 mL). The mixture was allowed to stir while white precipitate formed. The precipitate was collected by filtration and the solid was washed with methyl-tert-butyl ether (2×2 mL) and dried under high vacuum. The crude product was purified by semi-preparative RP-chromatography using gradient of ACN in 0.1% AcOHaq. 3'-O—(N-Acetone oxime)-8-aza-2'-deoxyguanosine was obtained as a white solid (0.3 g, 68%).

$^1$H NMR (DMSO-d6, 400 MHz) δ7.03 (br s, 2H, —$NH_2$), 6.38 (t, 1H, H-1'), 4.92-4.85 (m, 2H, OH-5', H3'), 4.10-4.08 (m, 1H, H4'), 3.98-2.90 (m, 1H, H5'), 3.60-3.52 (m, 1H, H5'), 3.13-3.06 (m, 1H, H2'), 2.60-2.52 (m, 1H, H2"), 1.86 (s, 6H, 2×—$CH_3$ of oxime).

Synthesis of 3'-(O)-Acetoxime-8-Aza-2'-Deoxyguanosine 5'-Triphosphate

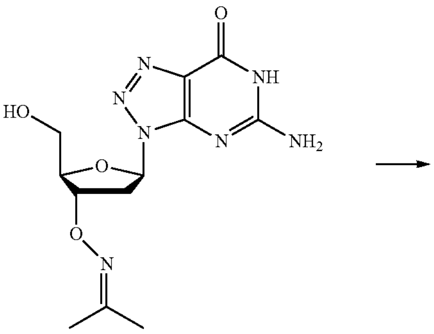

-continued

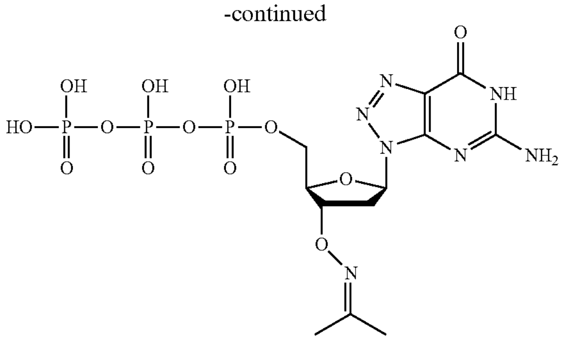

Lyophilised 3'-O—(N-acetone oxime)-8-aza-2'-deoxyguanosine (0.05 g, 0.15 mmol) was placed in flask, purged with nitrogen and dissolved in a mixture of anhydrous 1,4-dioxane (0.25 mL), DMF (0.25 mL) and pyridine (0.22 mL). A solution of 2-chloro-1,3,2-benzodioxaphosphorin-4-one (0.038 g, 0.19 mmol) in anhydrous 1,4-dioxane (0.25 mL) was added dropwise and allowed to stir at room temperature for 30 min. A solution of tributylammonium pyrophosphate (0.11 g, 0.2 mmol) in dry DMF (0.25 mL) and tributylamine (0.115 g, 0.6 mmol, 0.147 mL) was added to the reaction mixture and allowed to react at room temperature for 30 min. A precipitate formed during the addition, then redissolved. A solution of iodine (0.063 g, 0.25 mmol) in pyridine (1.3 mL) and water (0.03 mL) was added and the dark brown solution was stirred at room temperature for 10 minutes. The oxidizing solution was then quenched with a 10% sodium thiosulfate solution (~0.25 mL) while the brown colour discharged rapidly and solvents were removed under vacuum using rotary evaporator (the temperature of the water bath of the rotary evaporator was 35° C.). The oily residue was dissolved in water (10 mL) and the mixture was stirred for 15 min to hydrolyze the cyclic triphosphate moiety and then extracted with methyl-tert-butyl ether (2×2 mL). The aqueous phase was concentrated down to ~5 mL using a rotary evaporator (bath temperature 35° C.) and split into two falcon tubes (50 mL). A 2% solution of sodium perchlorate in acetone cooled to −80° C. (30 mL) was added to each when a white precipitate formed. Tubes were centrifuged for 15 minutes at 4000 rpm at −10° C. The pale yellow solution was decanted and the solid residue was dissolved in water (2×2.5 mL) and the precipitation procedure was repeated one more time. The white solid residue was washed with acetone cooled to −80° C. (3×4 mL for each), air-dried, dissolved in water and combined in one fraction. The precipitated 3'-(O)-acetoxime-8-aza-2'-deoxyguanosine triphosphate sodium salt was purified by reverse phase C18-HPLC using preparative Phenomenex Kinetex C18 column (30×250 mm, 5 mm). Fractions containing isolated triphosphate were pooled, evaporated to dryness, co-evaporated with methanol (3×10 mL) and lyophilised from water to give 3'-(O)-acetoxime-8-aza-2'-deoxyguanosine triphosphate triethylamine salt as a white solid. The semi-purified triphosphate was next subjected to purification using preparative AEX-HPLC on a Source15Q column. Fractions containing isolated triphosphate were pooled, evaporated to dryness, co-evaporated with methanol (3×10 mL) and lyophilised from water. The obtained solid was purified again by reverse phase C18-HPLC using a preparative Phenomenex Kinetex C18 column (30×250 mm, 5 mm) to give 3'-(O)-acetoxime-8-aza-2'-deoxyguanosine triphosphate triethylamine salt as a white solid. The triphosphate was quantified by UV (260 nm, ext. coeff.=13900 $Lmol^{-1}$ $cm^{-1}$ to be 21 µmole.

$^1H$ NMR ($D_2O$, 400 MHz) δ6.44 (t, 1H, H-1'), 4.98-4.93 (m, 1H, H3'), 4.41-4.35 (m, 1H, H4'), 4.08-4.15 (m, 1H, H5'), 4.05-3.95 (m, 1H, H5'), 2.93-2.89 (m, 1H, H2'), 2.62-2.51 (m, 1H, H2"), 1.79, 1.86 (s, 6H, 2×—$CH_3$ of oxime).

31P NMR ($D_2O$, 400 MHz) δ−8.88 (d, 1P), −11.39 (d, 1P), −22.95 (t, 1P).

Enzymatic DNA Synthesis Reactions

Enzymatic N+20 nucleotide addition reactions were conducted on polymer-coated silica paramagnetic particles. Enzymatic DNA synthesis was performed on a ThermoFisher KingFisher sample purification system. Enzymatic DNA synthesis consists of cycles of addition solution (containing TdT, reversibly terminated nucleotide and a near-neutral extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc. all with appropriate counterions, such as $Cl^-$) and inorganic pyrophosphatase (e.g., the *Saccharomyces cerevisiae* homolog)), wash 1 solution (HEPES+5 mM EDTA at pH 8.00), deblock solution (sodium nitrite at pH 5.5), and wash 2 solution (HEPES at pH 7.20). The following sequences CTTCATGACGTAAGGCCGAT (Oligo A) and GCCGTCATGACTTAAGGATC (Oligo B) were synthesized in triplicate. DNA products were analysed by next-generation sequencing on an Illumina MiniSeq. Data showing the percent perfect sequences are shown in the following plots for synthesis of these sequences with reversibly terminated dG and reversibly terminated 8-aza-dG; other nucleotides are reversibly terminated dA, dC or dT. The products made with reversibly terminated 8-aza-dG show a lower level of percent perfect sequences to those made with dG. Addition of 8-aza-dG to dA, dC or dT terminated sequences shows a similar efficiency to dG, however additions of any nucleotide to 8-aza-dG terminated sequences are less efficient than to dG terminated sequences.

The invention claimed is:

1. A compound according to Formula (1a) or (1b):

(1a)

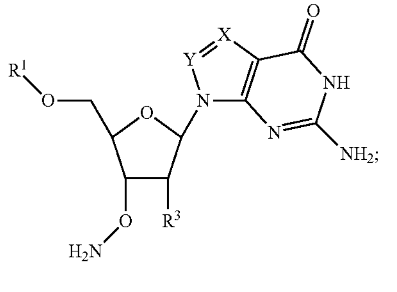

-continued (1b)

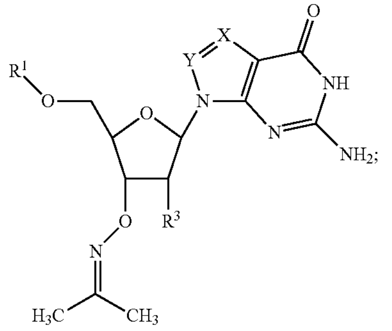

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either X is N and Y is N, or X is $CR^2$ and Y is CH or N, where $R^2$ is an electron withdrawing group (EWG) selected from the group consisting of: F, Cl, nitrile; halomethyl, dihalomethyl, trihalomethyl; $SOR^4$; $SO_2R^4$; $SO_3R^4$; $COR^4$; $CO_2R^4$; $CONR^4R^5$; wherein $R^4$ and $R^5$ are independently selected from H and $C_{1-6}$ alkyl optionally substituted with OH or halo atoms.

2. The compound according to claim 1 which is a compound of Formula (2a) or (2b):

(2a)

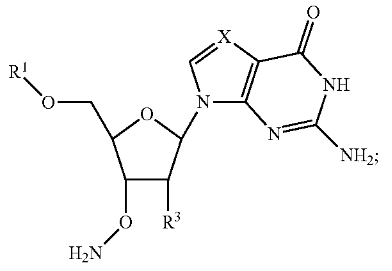

(2b)

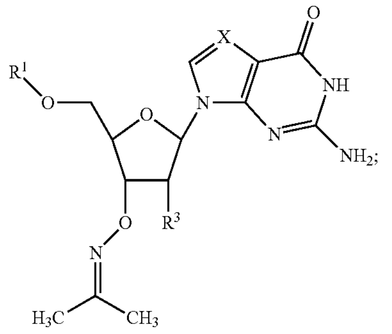

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and

X is $CR^2$, where $R^2$ is an electron withdrawing group (EWG) selected from the group consisting of: nitrile; halomethyl, dihalomethyl, trihalomethyl; $SOR^4$; $SO_2R^4$, $SO_3R^4$; $COR^4$; $CO_2R^4$; $CONR^4R^5$;

wherein $R^4$ and $R^5$ are independently selected from H and $C_{1-6}$ alkyl optionally substituted with OH or halo atoms.

3. The compound according to claim 1, wherein $R^2$ is nitrile, halomethyl, dihalomethyl or trihalomethyl.

4. The compound according to claim 3, wherein $R^2$ is F or Cl.

5. The compound according to claim 1, wherein $R^1$ is $—(PO_3)^-_x(PO_2S)^-_y(PO_3)^-_z$ where x, y and z are independently 0-5 and x+y+z is 1-5.

6. The compound according to claim 1, wherein $R^1$ is a monophosphate, diphosphate, triphosphate, tetraphosphate, pentaphosphate, or (alpha-thio)triphosphate group.

7. The compound according to claim 1, wherein $R^1$ is a triphosphate group.

8. The compound according to claim 1, wherein $R^3$ is H.

9. The compound according to claim 1 which is selected from the group consisting of

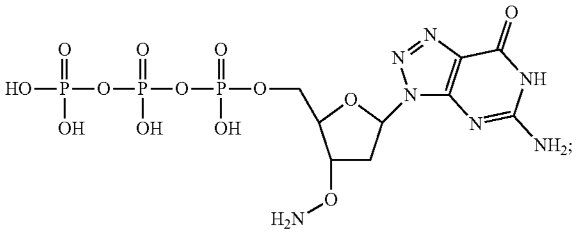

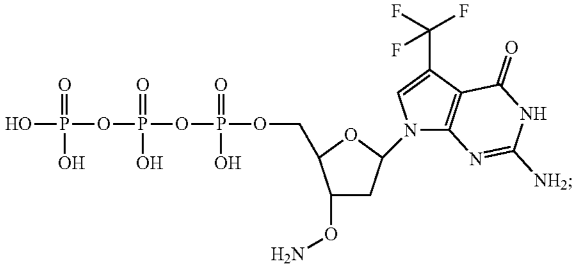

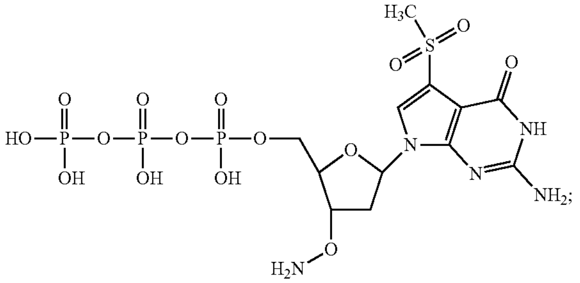

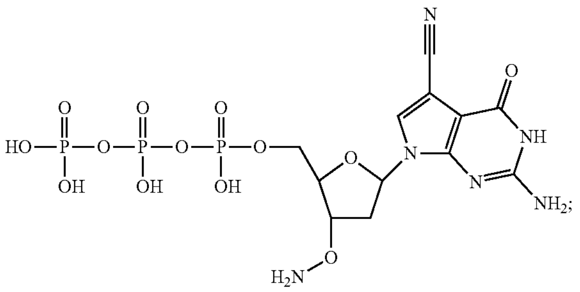

-continued

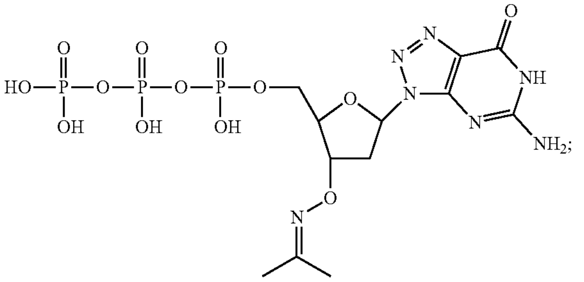

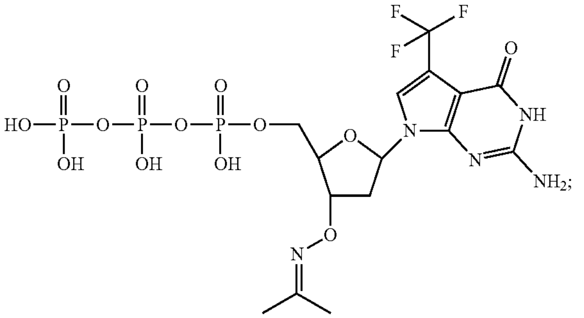

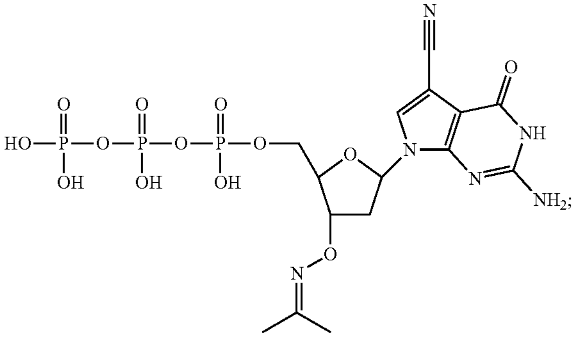

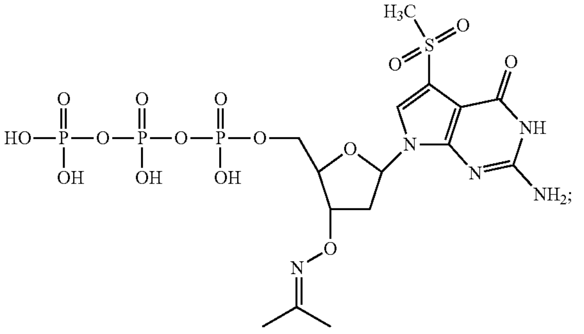

or a salt thereof.

10. A method of nucleic acid synthesis comprising reacting a compound according to claim 1 with an oligonucleotide in the presence of a polymerase or terminal deoxynucleotidyl transferase (TdT) enzyme and treating the extended oligonucleotide with a nitrite salt.

11. The method according to claim 10, wherein the oligonucleotide sequence is a solid-supported oligonucleotide sequence.

12. The method according to claim 9, wherein the nitrite salt is sodium nitrite.

13. A method of synthesizing a compound according to formula (1a):

(1a)

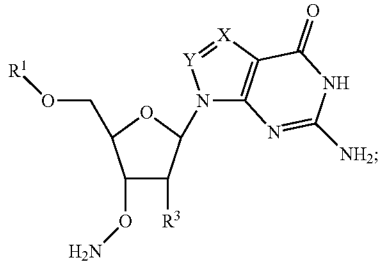

wherein $R^1$ is a phosphate or polyphosphate group or salt thereof, optionally containing one or more sulfur atoms;

$R^3$ is selected from H, OH, F, $OCH_3$, or $OCH_2CH_2OMe$; and either X is N and Y is N, or X is $CR^2$ and Y is CH or N, where $R^2$ is an electron withdrawing group (EWG) selected from the group consisting of: F, Cl, nitrile; halomethyl, dihalomethyl, trihalomethyl; $SOR^4$; $SO_2R^4$; $SO_3R^4$; $COR^4$; $CO_2R^4$; $CONR^4R^5$; wherein $R^4$ and $R^5$ are independently selected from H and $C_{1-6}$ alkyl optionally substituted with OH or halo atoms;

comprising taking a compound according to Formula (1b):

(1b)

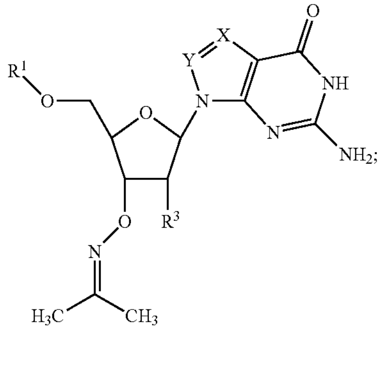

wherein, $R^1$ is a phosphate or polyphosphate group or salt thereof, optionally containing one or more sulfur atoms;

$R^3$ is selected from H, OH, F, $OCH_3$, or $OCH_2CH_2OMe$; and either X is N and Y is N, or X is $CR^2$ and Y is CH or N, where $R^2$ is an electron withdrawing group (EWG) selected from the group consisting of: F, Cl, nitrile; halomethyl, dihalomethyl, trihalomethyl; $SOR^4$; $SO_2R^4$; $SO_3R^4$; $COR^4$; $CO_2R^4$; $CONR^4R^5$; wherein $R^4$ and $R^5$ are independently selected from H and $C_{1-6}$ alkyl optionally substituted with OH or halo atoms;

and treating the compounds of Formula (1b) with an aminooxy compound.

14. The method according to claim 13 wherein the aminooxy compound is hydroxylamine, methoxylamine or ethoxylamine.

15. A kit comprising:

a. a compound according to claim 1;

b. a terminal deoxynucleotidyl transferase (TdT) enzyme; and c. a nitrite salt.

16. An oligonucleotide according to Formula (1a) or (1b):

(1a)

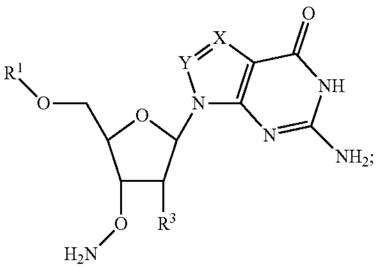

-continued (1b)

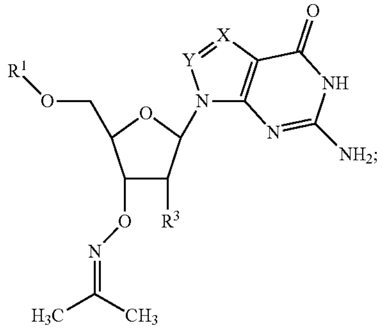

wherein, $R^1$ is an oligonucleotide;

$R^3$ is selected from H, OH, F, $OCH_3$, or $OCH_2CH_2OMe$; and either X is N and Y is N, or X is $CR^2$ and Y is CH or N, where $R^2$ is an electron withdrawing group (EWG) selected from the group consisting of: F, Cl, nitrile; halomethyl, dihalomethyl, trihalomethyl; $SOR^4$; $SO_2R^4$; $SO_3R^4$; $COR^4$; $CO_2R^4$; $CONR^4R^5$; wherein $R^4$ and $R^5$ are independently selected from H and $C_{1-6}$ alkyl optionally substituted with OH or halo atoms.

17. The oligonucleotide according to claim 16 wherein either Y is N and X is N; or Y is CH and X is $CR^2$ where $R^2$ is $SO_2CH_3$, CN or $CF_3$.

18. The oligonucleotide according to claim 16, wherein $R^3$ is H.

* * * * *